United States Patent [19]

Schlom et al.

[11] Patent Number: 5,698,530
[45] Date of Patent: Dec. 16, 1997

[54] RECOMBINANT VIRUS EXPRESSING HUMAN CARCINOEMBRYONIC ANTIGEN AND METHODS OF USE THEREOF

[75] Inventors: Jeffrey Schlom, Potomac; Judith A. Kantor, Rockville, both of Md.

[73] Assignee: The United States of America as represented by the Department of Health and Human Services, Washington, D.C.

[21] Appl. No.: 270,106

[22] Filed: Jul. 1, 1994

Related U.S. Application Data

[63] Continuation of Ser. No. 879,649, May 6, 1992, abandoned, which is a continuation of Ser. No. 695,024, May 6, 1991, abandoned.

[51] Int. Cl.$^6$ .......................... C12N 15/00; C07H 21/02; A61K 48/00
[52] U.S. Cl. ..................... 514/44; 536/23.1; 435/320.1; 435/172.3
[58] Field of Search .................. 514/44; 435/320.1

[56] References Cited

U.S. PATENT DOCUMENTS

| | | |
|---|---|---|
| 4,722,848 | 2/1988 | Paoletti et al. . |
| 5,017,487 | 5/1991 | Stunnenberg et al. . |

FOREIGN PATENT DOCUMENTS

| | | |
|---|---|---|
| 263933 | 4/1988 | European Pat. Off. . |
| 8901973 | 3/1989 | WIPO . |

OTHER PUBLICATIONS

Estin et al., "Recombinant Vaccinia Virus Vaccine Against the Human Melanoma Antigen p97 for Use in Immunotherapy," Proc. Natl. Acad. Sci. USA 85:1052–1056 (Feb., 1988).

Kuroki et al., "Serologic Mapping and Biochemical Characterization of the Carcinoembryonic Antigen Epitopes Using Fourteen Distinct Monoclonal Antibodies," Int. J. Cancer, 44:208–218 (1989).

Catalogue of Animal Viruses and Antisera, Chlamydiae and Rickettsiae, Eds. Buck & Paulino, 6th Ed., pp. 135–141 (1990).

Robbins et al., "Transduction and Expression of the Human Carcinoembryonic Antigen Gene in a Murine Colon Carcinoma Cell Line," Cancer Res. 51:3657–3662 (Jul. 15, 1991).

Kaufman et al., "A Recombinant Vaccinia Virus Expressing Human Carcinoembryonic Antigen," Int. J. Cancer, 48:900–907 (Jul. 30, 1991).

Oikawa, et al., 1987, Biochem Biophys Res Comm 142(2):511–518.

Muraro, et al., 1985, Cancer Research 45:5769–5780.

Mackett, et al., 1982, PNAS 79:7415–7419.

Lathe, et al., 1987, Nature 326:878–880.

Hosokawa, et al., 1988, Cancer Immunol. Immunother. 26:250–256.

Thummel, et al., 1981 Cell 23:825–836.

Sarser, et al. 1981, Molecular and Cellular Biology 1(6):486–496.

Tsary et al. JNET 87(13): 982, 1995.

Primary Examiner—Suzanne E. Ziska
Attorney, Agent, or Firm—Sewall P. Bronstein; Ronald I. Eisenstein; David S. Resnick

[57] ABSTRACT

The present invention relates to a recombinant carcinoembryonic antigen (CEA)/vaccinia virus or other viral vector which expresses CEA on the surface of infected cells and which elicits an immune response in vivo directed against CEA or cells expressing CEA and a pharmaceutical composition containing same. The invention also relates to methods of treating patients having tumors in which CEA is expressed and methods of stimulating the immune system against CEA.

35 Claims, 13 Drawing Sheets

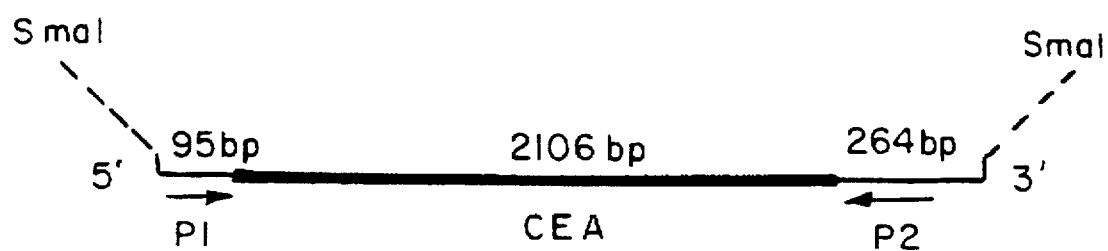
FIG. IA
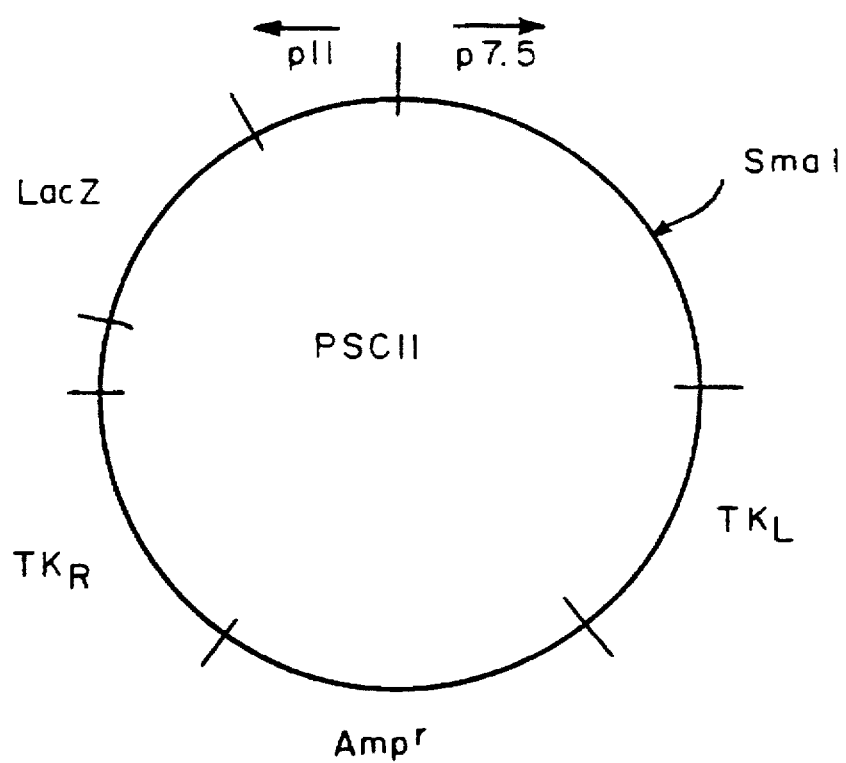
FIG. IB

RECOMBINANT VIRUS EXPRESSING HUMAN CARCINOEMBRYONIC ANTIGEN AND METHODS OF USE THEREOF

RELATED CASES

This is a continuation of application Ser. No. 07/879,649, filed May 6, 1992, now abandoned, which is a continuation of Ser. No. 07/695,024 filed May 5, 1991, now abandoned.

BACKGROUND OF THE INVENTION

1. Field of the Invention

The present invention relates, in general, to a recombinant virus. In particular, the present invention relates to a recombinant vaccinia or other viral vectors into which carcinoembryonic antigen is inserted and methods for use thereof to induce an active immune response.

2. Background Information

Carcinoembryonic antigen (CEA) is a highly glycosylated, 180,000-dalton protein which is expressed on most gastrointestinal carcinomas, including a large number of primary and metastatic colorectal tumors, and is also found on some normal endodermally derived tissues, though in much lower concentrations.

CEA was first described in 1965, although the gene was not isolated, nor its sequence determined until 1987 (see Oikawa et al., *Biochem. Biophys. Res. Comm.* 142:511–518 (1987)). CEA is one of the most widely studied of the oncofetal tumor-associated antigens. CEA has been used clinically in the surveillance of post-operative patients following primary tumor resection. Additionally, anti-CEA monoclonal antibodies (MAbs) have been used successfully in the diagnostic imaging of primary colon tumors, and in the immunolocalization of metastatic disease (see, e.g., Sikorska et al., *Cancer Det. Prev.* 12:321355 (1988); Goldenberg et al., "Cancer diagnosis and therapy with radiolabeled antibodies. In: C. W. Vogel (ed.), *Immunoconjugates: Antibody Conjugates in Radioimaging and Therapy of Cancer,* pp. 259–280. New York: Oxford University Press, 1987; Mach et al., *Immunol. Today* 2:239–249 (1981)).

While CEA is generally considered to be only weakly immunogenic in humans (no evidence of humoral or cell-mediated immunity to CEA in normal or cancer patients has been found), the present invention relates to the co-presentation of CEA with a strong immunogen to induce an anti-CEA response in vivo, e.g., in tumor immunotherapy.

Vaccinia virus is highly immunogenic and stimulates both humoral and cell-mediated responses; it is also capable of presenting tumor antigens with major cellular histocompatibility complex antigens. In addition, the use of recombinant vaccinia virus in vivo is advantageous due to its safety, efficacy, and cost. The virulence of the virus can be reduced by using different strains of the virus; deletion of the viral thymidine kinase (TK) gene or portions thereof also results in a much attenuated vaccinia virus; the virus is stable for long periods of time and can be easily administered to large populations; the cost of developing a vaccinia-vectored vaccine is less than that for many other methods of vaccine development; and, recombinant vaccinia virus can be used in individuals previously exposed to the vaccinia virus without decreasing the immunogenicity of the antigen co-presented therewith.

Recombinant vaccinia virus constructs have been prepared and effectively employed in the past against a variety of infectious diseases including hepatitis B, herpes simplex virus, parainfluenza type 3, and Lassa fever virus (Moss et al., *Nature* 311:67–69 (1984); Wachsman et al., *Biosci. Rep.* 8:323:334 (1988); Spriggs et al., *J. Virol.* 62:1293–1296 (1988); Fisher-Hoch et al., *Proc. Nat. Acad. Sci. USA* 86:317–321 (1989), respectively). Tumor challenge protection has also been demonstrated in animal models using recombinant vaccinia viruses as well (see Lathe et al., *Nature* (London) 326:878–880 (1987); Bernards et al., *Proc. Nat. Acad. Sci. USA* 84:6854–6858 (1987); Estin et al., *Proc. Nat. Acad. Sci. USA* 85:1052–1056 (1988)).

The present invention provides methods of treating carcinomas which express the CEA protein, including gastrointestinal and other CEA expressing carcinomas, comprising the use of a recombinant CEA-vaccinia virus. "Treating carcinomas" is defined as stimulation of the immune system against carcinoma cells expressing CEA via administration (immunization or vaccination) to a patient of a recombinant CEA/vaccinia virus which elicits an immune response to CEA.

SUMMARY OF THE INVENTION

This invention relates to recombinant viruses which express the human tumor-associated antigen CEA, and to methods of use thereof. Viral constructs made according to this invention express a protein product (CEA) which is recognized by anti-CEA monoclonal antibodies. Additionally, the recombinant virus elicits a humoral immune and/or cell mediated response against CEA when used in vivo.

A preferred embodiment of this invention comprises a recombinant CEA-vaccinia virus designated RV-CEA constructed by inserting a 2.4 kilobase (kb) Sma I restriction endonuclease fragment of CEA (comprising the complete coding sequence for CEA—A coding region of 2,106 nucleotides including a portion of both the 5' and 3' untranslated regions) into a vaccinia virus genome via homologous recombination. The resulting virus expresses CEA on the surface of infected cells.

As another aspect of this invention, it is contemplated that the RV-CEA construct, or another vaccinia virus-CEA construct made according to the general principles disclosed herein, will serve as a therapeutic agent in the treatment of human carcinomas which express CEA.

BRIEF DESCRIPTION OF THE DRAWINGS

FIG. 1 is a schematic diagram of the PSC 11-CEA plasmid construct. A Sma I restriction site for insertion of foreign genetic segments is in juxtaposition to the vaccinia p7.5 promoter aligning the viral promoter with the start site of the cloned gene. The *E. coli* LacZ gene coding for beta galactosidase is under the regulation of the vaccinia virus p11 promoter. The LacZ gene and the Sma I cloning site are both contained within segments of the right (TK-R) and left (TK-L) vaccinia thymidine kinase (TK) gene sequences. These viral sequences direct the insertion of the recombinant plasmid into the wild-type vaccinia TK gene. Vaccinia TK is a non-essential viral gene, and homologous recombination with the pSC 11 cloning plasmid results in a TK-deficient virus (FIG. 1A). The insert gene segment is a CDNA clone of CEA containing 95 base pairs of the 5' untranslated region, 264 base pairs of the 3' untranslated region, and 2,106 base pairs of coding sequences. $P_1$ and $P_2$ are primers used for PCR DNA amplification. The cDNA was blunt-end ligated into the pSC-11 Sma I cloning site (FIG. 1B). The resulting chimeric construct, designated PSC 11-CEA, was oriented by restriction endonuclease mapping with Bam H1.

FIG. 2 illustrates recombinant vaccinia-CEA-induced plaques. The tissue culture plates show a confluent monolayer of HuTK 143B cells infected with (A) wild-type virus, V-WR, or (B) the recombinant vaccinia-CEA virus, rV-CEA. The vital infection was propagated in media supplemented with 25 µl/ml BUDR and 300 µg/ml X-Gal. Recombinant viruses produce obvious blue plaques under these conditions.

FIG. 3 is a Southern blot analysis of recombinant vaccinia-CEA virus. V-WR and rV-CEA digested with Hind III hybridized with (A) a radiolabeled vaccinia virus DNA probe or (B) a radiolabeled beta galactosidase DNA probe. Southern blot (A) shows the lack of the 5.1 kilobase (kb) Hind III J fragment in the rV-CEA construct. Southern blot (B) shows the presence of a 9.2 kilobase (kb) Hind III fragment containing the beta-galactosidase gene representing the recombinant plasmid construct in the vaccinia Hind III J fragment.

FIG. 4 illustrates the detection of recombinant virus by direct plaque hybridization. (A) V-WR, (B) rV-CEA, or (C) recombinant vaccinia-beta-galactosidase virus were lifted from a cell monolayer onto a nylon membrane and hybridized to a radiolabeled CEA probe.

FIG. 5 is a polymerase chain reaction (PCR) analysis of recombinant vaccinia-CEA. Viral plaques were toothpicked and subjected to PCR analysis using primers constructed from the 5'- and 3'- end of the CEA gene. Aliquots of the PCR reaction were electrophoresed, blotted onto a nylon membrane, and hybridized to a radiolabeled CEA probe. Lane 1, CEA-positive control; lanes 2–9, individual recombinant vaccinia (rV-CEA) vital isolates; lane 10, wild-type (V-WR).

FIG. 6 shows the immunologic detection of CEA in cells using anti-CEA MAb COL-1 in immunofluorescent staining and the corresponding light photomicrographs of a cell monolayer infected with vaccinia virus. Panel (A) is a light photomicrograph of recombinant vaccinia (rV-CEA)-infected HuTK-143B cells. Panel (B) is the immunofluorescent staining of HuTK-143B cells infected with recombinant vaccinia (rV-CEA) and treated with the MAb COL-1. Panel (C) is a light photomicrograph of wild-type (V-WR)-infected HuTK 143B cells. Panel (D) is the immunofluorescent staining of wild-type (V-WR)-infected cells with MAb COL-1. Panel (E) is a light photomicrograph of recombinant vaccinia (rV-CEA)-infected HuTK143B cells. Panel (F) is the immunofluorescent staining of recombinant vaccinia (rV-CEA)-infected HuTK 143B cells treated with the MAb B72.3.

DETAILED DESCRIPTION OF THE SPECIFIC EMBODIMENTS

Figure 7:
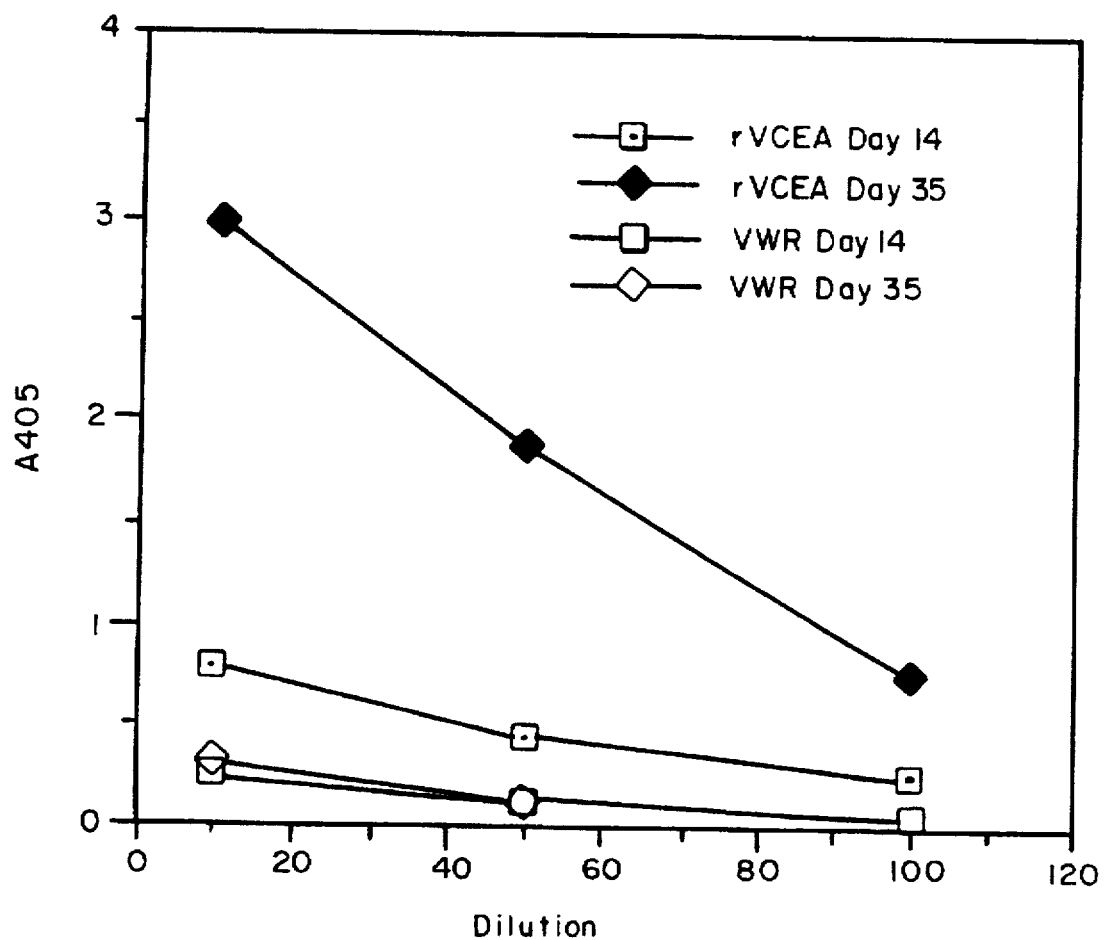
FIG. 7 compares the anti-CEA antibody response in mice immunized with wild-type and recombinant CEA-vaccinia virus. Eight week-old C57/BL6 female mice, 10 per group were immunized 3 times at 14-day intervals by intraperitoneal injection of 100 µl of crude lysate containing $1 \times 10^8$ pfu of vaccinia virus (V-WR) or its recombinant derivative (rV-CEA). Serum samples were collected 2 weeks after the primary immunization and 1 week after the third immunization. Anti-CEA antibody was quantitated by enzyme-linked immunosorbent assay (ELISA).

The present invention relates to a recombinant virus comprising a vaccinia or other viral vectors into which carcinoembryonic antigen (CEA) is inserted which recombinant virus expresses CEA or an antigenic fragment thereof on the surface of cells infected therewith and which recombinant virus elicits an immune response in vivo directed against CEA and cells expressing CEA. Preferably, the vaccinia virus is of a V-WR or NYC strain into which DNA coding for CEA or immunogenic fragment thereof is inserted or recombined, or other attenuated human vaccinia virus strains may be used. The preparation of recombinant vaccinia preparations for use as immunogens is described in, for example, U.S. Pat. Nos. 4,722,848 and 5,017,487, and in PCT publication WO 87/022038, which are incorporated herein by reference. The vaccinia virus may contain a promoter which increases CEA expression, e.g., synthetic late promoter of the plasmid PMJ601 (Davison, A. J. & Moss, B., Nucl. Acids Res. 18:4285–4286 (1990)). Other viral vectors may also be used, as will be apparent to the skilled artisan. These include, for example, baculovirus (described in, e.g., EPO publication EP 228 036), human adenovirus, SV40, fowlpox, or bovine papilloma virus into which DNA coding for CEA or the desired immunogenic portion thereof is inserted. Other vectors for use in the present invention include those of Salmonella (e.g., *Salmonella typhi*) and bacille Calmette Guerin, which is described in Stover et al., *Nature* 351:456–460 (1991) and incorporated herein by reference.

Additionally, the CEA can comprise a single or multiple immunodominant T-cell epitope. A CEA/vaccinia virus consisting of RV-CEA has been deposited with the ATCC and given accession no. VR 2323. The CEA sequence is described in Oikawa et al., *Biochem. Biophys. Res. Comm.* 142:511–518 (1987) and characterization of cDNA clones encoding human CEA is described in Zimmerman et al., *Proc. Natl. Acad. Sci.* 84:2960–2964 (1987), which are incorporated herein by reference. For purposes of the present invention, the sequences can be derived from the whole or antigenic portions of the CEA sequence. The nucleotide or amino acid sequences may be altered or antigenic portions identified and inserted in the recombinant vaccine preparations of the invention in accordance with techniques familiar to those of skill in the art.

In another embodiment, the present invention relates to a pharmaceutical composition comprising the above-described recombinant virus, and a pharmaceutically acceptable diluent, carrier, or excipient. The pharmaceutical composition of the invention includes the recombinant CEA/vaccinia virus in a quantity selected depending on the route of administration. Preferred routes of administration include intravenous, intraperitoneal, dermal abrasion, oral, subcutaneous, or intradermal routes. One skilled in the art will appreciate that the amounts to be administered for any particular treatment protocol can be readily determined. Suitable amounts might be expected to fall within the range of $10^5$ pfu to $10^9$ pfu.

In another embodiment, the present invention relates to a method of treating a carcinoma bearing patient wherein cells of the carcinoma express CEA comprising administering to the patient the above-described recombinant virus. More specifically, the cells of the carcinoma are gastrointestinal, breast, pancreatic, bladder, ovarian, lung, or prostate carcinoma cells or are epithelial derived carcinomas expressing CEA epitopes. In one preferred embodiment, the above-described method further comprises administering with the recombinant virus a biological response modifier. Preferably, the biological response modifier is selected from the group consisting of interleukin-2 (IL-2), interleukin-6 (IL-6), interferon, tumor necrosis factor (TNF), and cyclophosphamide, the preparation or availability of which are known to those of skill in the art. For example, the preparation of recombinant human IL-2 is described in detail in U.S. Pat. Nos. 4,738,927 and 4,992,367, and the expression of TNF is described in detail in U.S. Pat. No. 4,650,674, each of which is incorporated herein by reference. The above-described method can further comprise administering with the recombinant virus an adjuvant. One skilled in the art will appreciate that the amounts to be administered for any particular treatment protocol can readily be determined. Suitable adjuvants include, but are not limited to, mineral gels, e.g., aluminum hydroxide, alum, surfaceactive substances such as lysolecitihin, pluronic polyols, polyanions, peptides, oil emulsions and the like.

In a further embodiment, the present invention relates to a method of stimulating the immune system of a mammal against CEA for the purpose of preventing the establishment and growth of carcinoma cells comprising administering to the mammal the above-described recombinant virus in an amount sufficient to effect said stimulation. The vaccinia virus can be of the NYC strain, or recombined with an attenuated human vaccinia virus strain. In one preferred embodiment, the above-described method further comprises administering with the recombinant virus a biological response modifier (preferably, the biological response modifier is selected from the group consisting of interleukin-2 (IL-2), interleukin-6 (IL-6), interferon, tumor necrosis factor (TNF), and cyclophosphamide). The above-described method can also further comprise administering with the recombinant virus an adjuvant. One skilled in the art will appreciate that the amounts to be administered for any particular treatment protocol can readily be determined. The preferred routes of administration are as described above.

The present invention is described in further detail in the following non-limiting examples.

EXAMPLE 1

Construction of Recombinant vaccinia Virus-CEA

Recombinant vaccinia viruses were constructed generally as described by Mackett et al., ("The construction and characterization of vaccinia virus recombinants expressing foreign genes." In: D. M. Glover (ed.) *DNA Cloning; A Practical Approach*, pp. 191–211. Oxford Press (1985)). Specifically, a human CEA cDNA clone was isolated from a human colon tumor cell library. Poly A+ RNA from GEO cells (Laboratory of Tumor Immunology and Biology, NCI) was isolated, cDNA synthesized by reverse transcription and made double stranded by DNA polymerase. Linkers containing the restriction enzyme sites, Hind III and Bam H1 were ligated to the cDNA and inserted into the directional cloning vector lambda orf-8 (according to the methods described by Meissner et al., PNAS 84:4171–4175 (1987)). Recombinant plaques containing CEA were detected using nucleic acid hybridization procedures. Positive plaques were purified and sequenced. A 2.8 kilobase (kb) clone was found to contain the entire coding region of CEA (2,106 nucleotides), over 100 nucleotides of the 5' untranslated region, including the poly A° tail. A 2.4 kilobase (kb) Sma I fragment was isolated from this clone and blunt-end ligated into the Sma I restriction site of the donor plasmid pSC-11. Orientation of the plasmid insert was determined by Bam HI endonuclease digestion and analysis. The resulting plasmid construct was designated PSC 11-CEA (FIG. 1).

Homologous recombination of PSC 11-CEA with vaccinia virus having a non-essential TK gene in the Hind III J fragment of the viral chimeric virus (.see Mackett et al., Id.; PNAS 79:7415–7419 (1982)). The presence of the PSC 11-CEA LacZ gene coding for beta-galactosidase in the recombinant virus provided a method for selection.

The recombinant virus rV-CEA was constructed as follows: a 60-mm tissue culture dish of nearly confluent CV-1 cells, African Green monkey kidney cells (ATCC No. CCL 70) was infected with approximately 0.20 plaque-forming units/cell (pfu/cell) of V-WR for approximately two hours at 37° C. While infection was in progress, a pSC 11-CEA DNA precipitate was prepared using 1 milliliter (ml) of transinfection buffer (0.14M NaCl, 5 mM KCl, 1 mM $Na_2HPO_4$, 0.1% dextrose, and 20 mM HEPES (4 [2-hydroxethyl]-1-piperazine-ethanesulfonic acid), pH adjusted to 7.0–7.1, 5 µg chimetic pSC 11-CEA plasmid DNA, and 1 ug vaccinia virus DNA, as carrier. This solution was mixed and approximately 50 µl of 2.5M $CaCl_2$ was added, the mixture agitated gently and stored at room temperature for approximately 20 minutes while the DNA precipitated.

After infection, the viral inoculum was aspirated off the CV-1 monolayer which was then rinsed twice with 1× phosphate buffered saline (PBS). The DNA precipitate was added to the CV-1 monolayer in a dropwise fashion and left on the cells at room temperature for approximately 30 minutes, whereupon 5 ml of fresh culture medium (Dulbecco's medium; Gibco/BRL) supplemented with 5% fetal calf serum (FCS) was added and the cells incubated at 37° C. for about three hours. The media was then aspirated from the dish and replaced with 5 ml of fresh media supplemented with 5% FCS, and the cells again incubated at 37° C., this time for approximately 48 hours.

Following incubation, the cells were scraped into the culture media and collected via centrifugation. The cell pellet was resuspended in 0.5 ml of MEM (Minimal Essential Media; Gibco/BRL). The progeny virus were released from the cells by three cycles of freeze-thawing, followed by sonication of the cells for approximately 1 minute in a 450-watt water bath sonicator.

The progeny virus, as well as wild-type V-WR control, were plated on confluent monolayers of HuTK⁻143B cells, a human osteosarcoma cell line with a deficient thymidine kinase gene (ATCC No. CRL 8303), in the presence of 25 µg/ml 5-bromodeoxyuridine (BuDR; obtained from Boehringer Mannheim Biochemicals) and 300 µg/ml 5-bromo-4-chloro-3-indoyl-beta-D-galactosidase (X-Gal; Gibco/BRL). Recombinant viral clones were selected by growth on the HuTK⁻143B cells as evidenced by the formation of blue plaques (FIG. 2B).

The plaques were next isolated and the progeny virus purified by five rounds of plaque purification using selection conditions similar to those described above. High-titer lysates of the purified viral isolates were prepared by successive passage in tissue culture flasks according to standard techniques (see Mackett et al., (1982), supra). In general, titers of $1 \times 10^8$ pfu/mi to $1 \times 10^9$ pfu/ml were obtained. Viral stocks were stored at −70° C.

EXAMPLE 2

Testing

Recombinant vaccinia virus-CEA DNA was extracted and the viral genomes analyzed by Hind III restriction endonuclease digestion and Southern blotting. For purposes of this discussion, reference will be made only to the preferred recombinant vaccinia virus-CEA isolate, rV-CEA.

To obtain samples of recombinant and wild-type control viral DNA, nearly confluent monolayers of HuTK⁻143B cells were infected with approximately 30 pfu/cell of V-WR or rV-CEA, generally as described above. The infections were allowed to proceed until maximal cytopathic effect was observed, about 24 hours, whereupon the cells were scraped into the culture media, pelleted by centrifugation, and resuspended in about 50 µl of 1× PBS.

To each sample, 300 µl of low salt buffer (20 mM Tris-HCl, [Tris (hydroxymethyl) aminomethane] buffered to pH 8.0, 10 mM EDTA (ethylenediamine tetra-acetic acid), and 0.75% SDS (sodium dodecyl sulfate) and 20 µl of proteinase K (10 mg/ml from Boehringer Mannheim Biochemicals was added and mixed. The mixture was incubated overnight at 37° C., with shaking, extracted twice with a mixture of phenol/chloroform and twice with chloroform alone. Sodium acetate pH 5.0, was added to 0.3N and two volumes of ethanol were added to precipitate the DNA. The DNA was collected by centrifugation and washed 2× with 70% ethanol, dried and analyzed as described below.

EXAMPLE 3

Restriction Endonuclease Analysis

V-WR and rV-CEA DNA was digested with Hind III endonuclease according to the manufacturer's instructions (Gibco/BRL), electrophoresed on a 0.6% agarose gel at 45 volts overnight, the DNA transferred to a BIOTRAN® nylon membrane (ICN) and hybridized with a $p^{32}$-dCTP-labeled vaccinia virus DNA probe. Vaccinia virus DNA was isolated according to this established procedure. 20 $A_{260}$ units of purified wild type vaccinia virus (≈50 µg) was brought to a final volume of 1.2 ml in 50mM Tris-HCl; pH 7–8 [Tris (hydroxymethyl) aminomethane]. To this solution was added 0.1 ml of 10% SDS (sodium dodecyl sulfate), 0.2 ml 60% sucrose, 0.4 ml of Proteinase K (10 mg/ml; Boehringer Mannheim Biochemicals) and incubated at 37° C. for 4 hours. This solution was extracted twice with an equal volume of phenol equilibrated with 50mM Tris-HCl pH 7–8 and once with phenol/chloroform (1:1). One tenth the volume of 1M sodium acetate (pH 7.0) and 2.5 volumes of ethanol were added and the DNA was allowed to precipitate at −20° C. overnight. The DNA was collected by centrifugation, the supernatant aspirated, and the pellet washed with 95% ethanol and air dried. The dried pellet was resuspended in 100 µl $H_2O$ and the concentration determined by absorbance at 260 nm. Twenty five ng of this DNA was labeled with $P^{32}$-dCTP using Gibco/BRL Random Primers DNA Labelling System according to the manufacturers instructions. The filters were prehybridized overnight at 37° C. in 40% Formamide (Clonetech) and 5× Denhardts (0.1% Ficoll 400 (Sigma); 0.1% polyvinyl pyrrolidine (Sigma) and 0.1% BSA (Bovine Serum Albumin; Boehringer Mannheim Biochemicals); 3× SSC (0.45M NaCl; 0.045M sodium citrate), 2.5% dextran sulfate (Sigma) and 0.1 mg/ml denatured Salmon Sperm DNA (Lofstrand Laboratories). $1×10^6$ cpm/ml of denatured vaccinia virus dCTP labeled probe was added and hybridized at 37° C. overnight with agitation. The filter was washed 2× for fifteen minutes in 2× SSC and 0.1% SDS at room temperature and then 2× for fifteen minutes in 0.1× SSC, 0.1% SDS at 65° C. The blot was exposed to X-ray film for 4 hours, developed and analyzed for the presence of a 5.1 kilobase (kb) band corresponding to the wild type Hind III J fragment.

V-WR DNA revealed a typical vaccinia virus restriction pattern (see McCarron et al., *Virol.* 86:88–101 (1978)) including a 5.1 kilobase (kb) band corresponding to the Hind III J fragment. In contrast, rV-CEA DNA did not reveal the 5.1 Hind III band due to insertion of the chimeric plasmid construct into the viral TK gene.

As shown in FIG. 3A, a 5.1 kilobase (kb) Hind III J fragment in the wild type V-WR DNA hybridized with the vaccinia virus DNA probe. No corresponding band was found in the rV-CEA DNA in this size range. Thus, the rV-CEA DNA clearly lacks the 5.1 kilobase (kb) Hind III J fragment.

To determine the size of the recombinant J fragment, Southern blots containing Hind III-digested V-WR, rV-CEA, and human genomic DNA were hybridized with a $P^{32}$-dCTP-labeled probe to the *E. coli* beta-galactosidase gene. The polymerase chain reaction (PCR) was performed using two specific 20 base oligomers as primers (5'GGGAAAACCCTGGCGTTACC 3' and 5' TCGAAT-CAGCAACGGCTTGC 3') which bounded a 1 kilobase (kb) fragment of the beta-galactosidase gene. This was PCR'd from VSC 8, the 1 kilobase (kb) band was cut from a 0.8% agarose gel and labeled using the Gibco./BRL Random Primers Labeling System according to the manufactures instructions; sequence taken from Shapira, et al., Gene 25:71–82 (1983).

As shown in FIG. 3B, the beta-galactosidase gene is present in the recombinant virus as evidenced by the distinct band at 9.2 kb in the RV-CEA viral DNA blot. This result is consistent with the expected size of the recombinant Hind III J fragment. The beta-galactosidase gene is absent in the wild type vaccinia genome, and in the human genomic DNA.

EXAMPLE 4

Plaque Hybridization Analysis

The presence of the CEA gene in the recombinant vaccinia virus genome was determined by DNA hybridization and polymerase chain reaction (PCR) analyses.

In the hybridization study, nearly confluent monolayers of HuTK⁻143B cells grown in 60 mm tissue culture dishes were infected with approximately 10 pfu/cell rV-CEA, V-WR as a negative control, and recombinant vaccinia-beta-galactosidase virus (VSC 8; obtained from Dr. Bernard Moss, NIAID, Bethesda, Md.) as a positive control. VSC 8 is a recombinant vaccinia virus containing the *E. coli* LacZ gene inserted into the vaccinia TK gene (Chakrabarti et al., *Mol. Cell. Biol.* 5:3403–3409 (1985)). The infected cells were incubated at 37° C. for about 24 hours and following incubation the viral DNA was directly transferred to nylon membranes by application of the membrane directly over the cell monolayer for about 10 minutes. After the DNA transfer was complete, the membrane was removed from the plate, denatured, neutralized, and soaked in 2× SSC (0.3M NaCl, 0.03M sodium citrate) for several minutes. Next the DNA was cross-linked to the membrane by exposure to ultraviolet (UV) radiation for approximately 2 minutes using a DNA transfer lamp (Foto Dyne, New Berlin, Wis.). Following UV exposure, the membrane was hybridized with a $P^{32}$-dCTP-labeled CEA probe and exposed to X-ray film overnight. The CEA probe was a 560 base pair PST I fragment excised from the Vector pGEM 7 (Dr. John Shively, City of Hope, Duarte, Calif.). Twenty five ng of this fragment was labeled with $dCTP^{32}$ using the Random Primers Labeling System of Gibco/BRL according to the manufacturers instructions. The probe was hybridized to the blots as described above.

As shown in FIG. 4, the rV-CEA plaques (FIG. 4B) hybridized well to the CEA probe, whereas the V-WR (FIG. 4A) and the VSC 8 plaques (FIG. 4C) did not.

EXAMPLE 5

Polymerase Chain Reaction Analysis

For the PCR studies, nearly confluent monolayers of HuTK⁻143B cells were grown in 60 mm tissue culture dishes, infected with approximately 10 pfu/cell rV-CEA or V-WR, and incubated at 37° C. for about 24 hours. Following infection, the monolayers were covered with agarose overlays, thereby fixing the location of the viral plaques on the dish. Individual plaques were then isolated by toothpick transfer, placed in about 1 ml of 1×PBS, without calcium or magnesium, and boiled for approximately 10 minutes followed by cooling on ice.

Standard polymerase chain reaction (PCR) was performed according to the manufacturers instructions using the amplification kit supplied by Cetus Corp. For this study, oligonucleotide primers recognizing the full CEA cDNA segment were constructed for priming the PCR reaction, i.e., primers were constructed from the 5' and 3' end of the CEA gene (see FIG. 1A, $P_1$ and $P_2$). A wild-type vaccinia virus plaque was used as a negative control.

Following 30 cycles of viral amplification, samples of each plaque isolate were electrophoresed on a 1% agarose gel, transferred to a nylon membrane, and hybridized with the radiolabeled CEA probe as described above. The results are shown in FIG. 5. All recombinant isolates and the CEA positive control (lanes 1–9) hybridized with the CEA gene probe, whereas the wild-type vaccinia virus DNA (lane 10) failed to show any hybridization.

EXAMPLE 6

Protein Expression Analysis

CEA protein expression and localization were determined by immunofluorescent staining of V-WR and rV-CEA infected cells using MAb COL-1, a murine monoclonal antibody directed against, and reactive with CEA (Muraro et al., Cancer Res. 45:5769–5780 (1985)). To test for CEA protein expression, nearly confluent monolayers of HuTK$^-$ 143B cells were inoculated with 30 pfu/cell of V-WR or rV-CEA and incubated at 37° C. for approximately 5 hours. The viral inoculum was then aspirated off the cells and the monolayer washed 3 times with 1×PBS. The cells were then fixed for about 30 minutes at room temperature using a freshly prepared solution of 2% paraformaldehyde in PBS. After fixing, the cells were washed 3 times with Minimal Essential Media (MEM; Gibco/BRL) and "blocked" with 1% BSA in PBS for about 30 minutes.

Following the above treatment, the fixed, blocked cells were treated by the addition of 1 µg/ml of MAb COL-1 or MAb B72.3 (Laboratory of Tumor Immunology and Biology, NCI), a negative control murine antibody which is unreactive with CEA, and shaken at room temperature for about 1 hour. The cells were then washed 5 times with 1× PBS and fluorescent-conjugated goat anti-mouse second antibody (Kirkegaard and Perry Laboratories, Inc.) was added at a dilution of 1:100. After approximately 30 minutes, the cells were washed 5 times with 1× PBS and the expression and cellular localization of CEA determined by immunofluorescent microscope. Immunofluorescent staining was maximal within 5 hours of initial vital infection. Further incubation with virus led to cytolysis of infected cells and degradation of membrane protein.

As shown in FIG. 6A and B, cells infected with recombinant vaccinia (rV-CEA) showed distinct cell surface staining with MAb COL-1 under fluorescence, the recombinant vaccinia (rv-CEA) virus expressing CEA in the cellular membrane of infected cells consistent with the normal cellular localization of CEA. In contrast, cells infected with the wild-type vaccinia (V-WR) virus failed to show any immunofluorescent staining with COL-1 (FIG. 6C and D). Immunofluorescent staining with the isotype-matched negative control antibody B72.3 failed to elicit any imaging on cells infected with the recombinant vaccinia (rV-CEA) virus (FIG. 6E and F).

EXAMPLE 7

ELISA Analysis

Eight-week old C57/BL6 female mice (Frederick Cancer Research Facility), 10 per test sample, were inoculated three times at 14-day intervals by intraperitoneal (IP) injection with 100 µl crude lysate containing approximately 1×10$^8$ pfu wild-type (V-WR) or recombinant vaccinia (rV-CEA). Approximately two weeks after primary injection and one week after tertiary injection, blood was drawn from each mouse and the sera separated. As shown in Table 1, below, and FIG. 7, the mice developed antibody titers to CEA within approximately 14 days of inoculation, a response that was boosted with subsequent immunization.

TABLE 1

Immune Response to Human CEA Antigen and Vaccinia Virus Antigens in Mice Immunized with rV-CEA and V-WR

| Immunized with | CEA Antibody[a] | | VV Antibody[b] | |
|---|---|---|---|---|
| | 14 days | 35 days | 14 days | 35 Days |
| V-WR | <0.05 (0.009–0.09) | <0.03 (0.01–0.05) | ++ | +++ |
| rV-CEA | 1.56 (0.7–3.12) | 12.5 (6.25–50.0) | ++ | +++ |

[a]Anti-CEA antibody was expressed as the concentration (µg/ml) of CEA-specific MAb COL-1 needed to give an equivalent ELISA reactivity at A405. Numbers in parentheses are the ranges of 10 mice. Results shown are for sera collected 14 days after the first inoculation and 7 days after the third inoculation. Mouse antisera were diluted 1:100.
[b]Anti-vaccinia virus antibodies were detected in the standard ELISA assay and are expressed as equivalent A405 readings when compared with a standard curve of rabbit polyclonal antisera at dilutions of 1:20,000 (+++) and 1:30,000 (++). Mouse antisera were diluted 1:100.

Anti-CEA and anti-vaccinia virus antibody were quantitated in the sera by enzyme-linked immunosorbent assay (ELISA) as follows:

A 96-well microtiter plate was coated with 100 µl of wild-type (V-WR) antigen (i.e., approximately 1×10$^7$ viral particles) in 0.1M sodium carbonate buffer, pH 9.6, overnight. The plates were then blocked with 1% BSA in Tris buffered saline (TBS) containing 0.1% glutaraldehyde, washed 3× in PBS and incubated about 1 hour at room temperature with the mouse sera obtained above.

Mouse sera antibodies which bound to the vaccinia antigen V-WR were detected using the Immuno Select Kit from Gibco/BRL. This kit allows the detection of rabbit or mouse primary antibodies, either polyclonal or monoclonal, associated with antigens immobilized on a solid support. A biotinylated secondary antibody (goat anti-mouse) is bound to a streptavidin-alkaline phosphatase conjugate and this preformed complex is added to the ELISA plate following the primary antibody. The plates were washed with Tris buffered saline (TBS) and the resulting alkaline phosphatase complex is detected using the chromogen pNPP (p-nitrophenyl phosphate). The reaction was stopped by the addition of sodium hydroxide and sample absorbencies at 405 nm were read by an ELISA reader (Bio-Tek Microplate Reader, Model EL 310). A rabbit polyclonal antivaccinia antibody (provided by Dr. Mark Buller, NIAID, Bethesda, Md.) was used as a positive control on the anti-vaccinia plates.

Similar procedures were followed using CEA as the test antigen. 96-well microtiter plates were coated with 100 µl (250 ng) purified CEA protein (International Enzyme, San Diego, Calif.) and stored at 37° C. overnight. The plates were then blocked with 1% BSA in TBS. The ELISA procedure described above was then followed, except that MAb COL-1 was used as the positive control antibody.

The results of these tests were compiled and a standard curve prepared correlating the A405 readings to the amount of MAb COL-1 added. The amount of CEA-specific antibody present in each experimental sample was then calculated in MAb equivalents from the A405 readings in the linear range obtained with the appropriate dilutions and the anti-vaccinia antibody production was correlated with anti-CEA antibody production. The results of the study are summarized in FIG. 7.

In the ELISA test, the in vivo response of mice to the vaccinia virus itself was also measured by assaying for anti-vaccinia antibodies to ensure that the mice had been adequately immunized with the vaccinia virus. Table 1 shows the antibody response to the vaccinia virus and clearly demonstrates that the mice received an adequate inoculum of virus.

For this in vivo study, a control group of mice received $1 \times 10^8$, pfu/ml of wild-type vaccinia (V-WR) virus at 2 week intervals. These mice developed a similar antibody response to the vaccinia virus when compared with the recombinant virus (rV-CEA)-treated animals. The control animals did not develop an antibody response to CEA (Table 1; FIG. 7). None of the vaccinated mice exhibited any evidence of toxicity for the 42-day observation period following immunization.

These data suggest that inoculation with a recombinant vaccinia (rV-CEA) virus enables the immune system to recognize human CEA and to mount a humoral immune response against the antigen.

EXAMPLE 8

Therapy studies

Four to five week old female C57/BL6 mice obtained from the Frederick Cancer Research Facility were inoculated by subcutaneous injection of $2 \times 10^5$ MCA38 murine adenocarcinoma cells which had been transduced with the human CEA gene. These cells have been shown to express the human CEA gene containing COL-1 epitopes. Ten animals per group were inoculated by tail scarification 7 days after tumor implantation with 10 µl of crude lysate containing $1 \times 10^{10}$ pfu of wild type; V-WR or recombinant vaccinia, rV-CEA. The second and third immunizations were at 14 day intervals. Animals were checked weekly for the presence of tumor. Tumors were measured by caliper in two dimensions and the volume calculated using the formula: width$^2 \times$length+2.

Figure 8B:
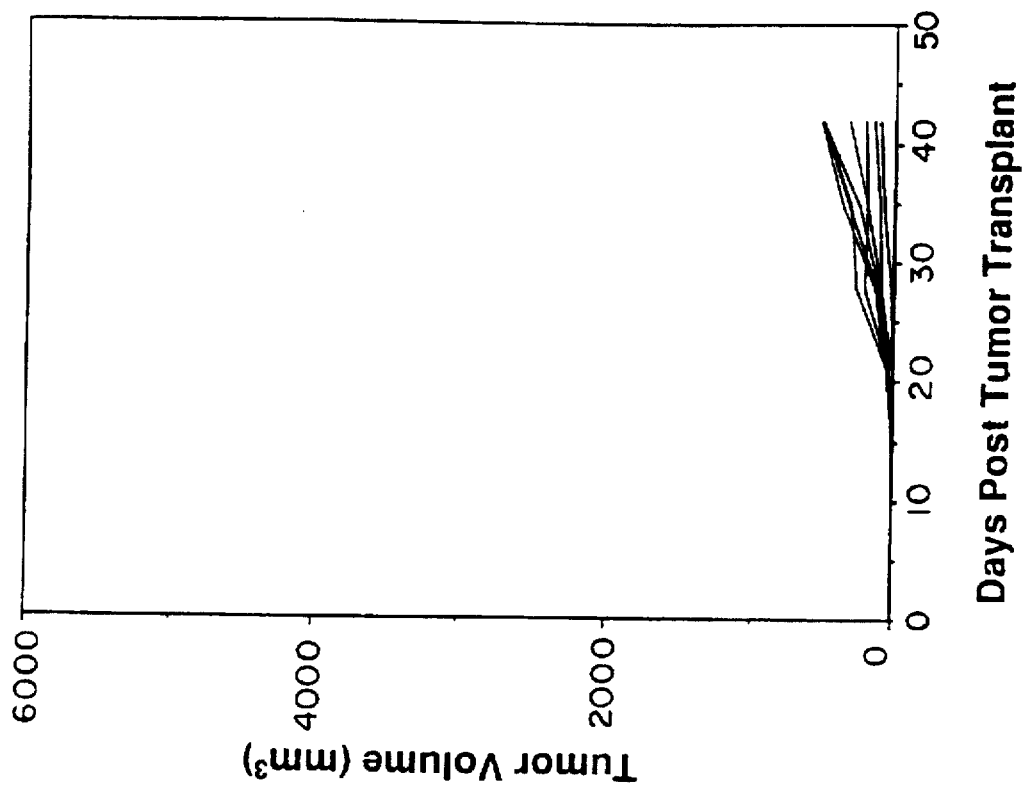
FIG. 8 shows the effect of administration of the recombinant CEA-vaccinia construct on the growth of a mouse adenocarcinoma cell line transduced with and expressing human CEA. Ten C57/BL6 female mice per group were injected subcutaneously with $2 \times 10^5$ murine colon carcinoma MCA38 tumor cells expressing CEA. Seven days later they were administered by tail scarification either 10 µl of $1 \times 10^{10}$ pfu of wild-type (V-WR) or recombinant (rV-CEA) vaccinia followed by two additional inoculations 14 days apart. Subcutaneous tumors were measured in two dimensions, weekly, and the volumes calculated by the formula: width$^2 \times$ length÷2. Panel (A) shows the growth of tumor of 10 individual mice inoculated with wild-type vaccinia (V-WR) virus. Panel (B) shows the growth of tumors of 10 individual mice inoculated with recombinant vaccinia (rv-CEA) virus containing human CEA.
Figure 8A:
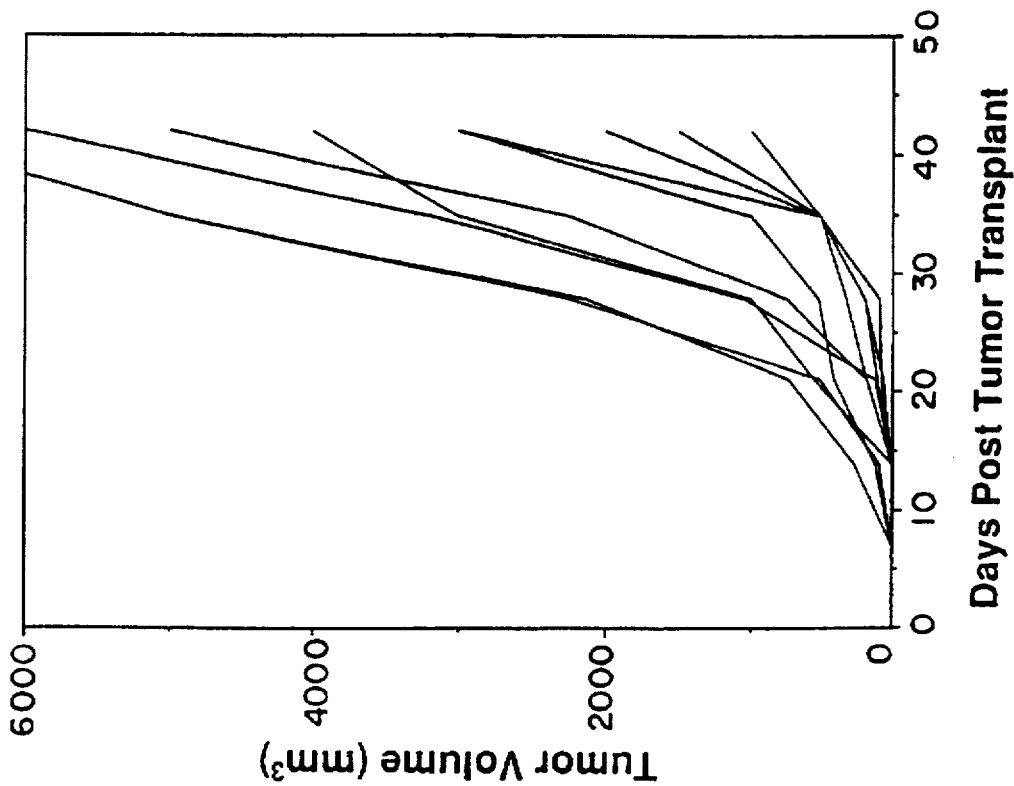

FIG. 8 shows the results of the growth of 7 day established subcutaneous tumors of 10 individual mice given either wild type vaccinia virus (V-WR; FIG. 8A) or recombinant vaccinia virus (rV-CEA, FIG. 8B). Animals that received the recombinant vaccinia virus containing human CEA experienced a dramatic reduction in tumor growth during the course of 42 days; moreover, two of the animals that received the recombinant vaccinia (rV-CEA) never developed tumor. These tumor-free animals were then rechallenged with $2 \times 10^5$ MCA38 CEA-transduced cells. After 90 days they continued to be tumor free. In contrast, animals administered wild type (V-WR) virus developed rapidly growing tumors. Animals receiving no vaccinia construct also developed tumors and their growth rate was similar to that of the animals administered wild type vaccinia (V-WR).

EXAMPLE 9

Prevention studies

Five to six week old female C57/BL6 mice obtained from the Frederick Cancer Research Facility were inoculated three times, fourteen days apart with 10 µl of crude lysate containing $1 \times 10^{10}$ pfu of virus. Ten animals per group received either the wild type vaccinia (V-WR) virus or recombinant vaccinia (rV-CEA) virus. Two days after the last immunization, $2 \times 10^5$ MCA38 murine adenocarcinoma cells which had been transduced with the human CEA gene were transplanted, subcutaneously into the mice. Animals were checked weekly for the presence of tumor. Tumors were measured by caliper in two dimensions and the volumes calculated using the formula: width$^2 \times$length+2.

Figure 9B:
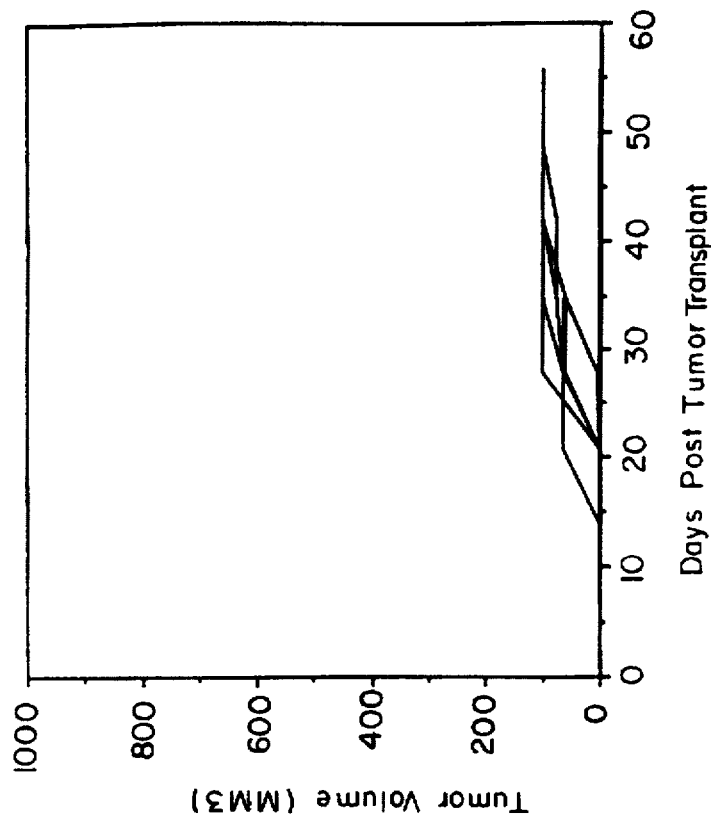
FIG. 9 illustrates the prevention of the subcutaneous growth of a mouse adenocarcinoma cell line transduced with and expressing human CEA after three immunizations using the recombinant CEA vaccinia construct. Ten C57/BL6 female mice per group were immunized by tail scarification with 10 µl of crude wild-type vaccinia (V-WR) or the recombinant vaccinia (rV-CEA). Each immunization was administered 14 days apart. Vaccinations were administered at days −30, −16, −2. Two days following the last immunization $2 \times 10^5$ MCA38 colon carcinoma cells expressing human CEA were transplanted subcutaneously. Panel (A) shows the growth of tumor of 10 individual animals immunized with wild type (V-WR) virus. Panel (B) shows the growth of tumors of 10 animals immunized with recombinant vaccinia (rV-CEA) virus containing human CEA.
Figure 9A:
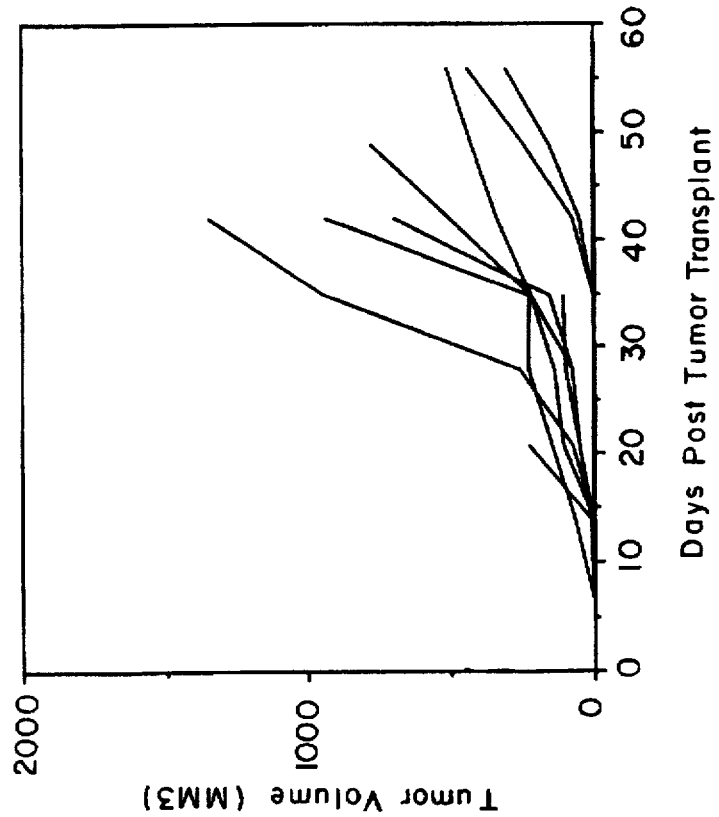

FIG. 9 shows the results of the growth of subcutaneous tumors of 10 individual mice after three immunizations of either wild type vaccinia virus (V-WR; FIG. 9A) or recombinant vaccinia virus (rV-CEA; FIG. 9B). Not only was there a dramatic reduction in tumor growth, but immunizations with recombinant vaccinia (rV-CEA) delayed the onset of the growth of the tumors by 7–10 days. In contrast, animals given wild type virus (V-WR) had rapidly growing tumor throughout the 56 day observation period.

EXAMPLE 10

Therapy with vaccinia and cyclophosphamide

Four to five week old female C57/BL6 mice obtained from the Frederick Cancer Research Facility were treated with cyclophosphamide (100 mg/kg) by intraperitoneal injection. Two days following this injection, $2 \times 10^5$ MCA38 murine adenocarcinoma cells which had been transduced with the human CEA gene were transplanted by subcutaneous injection. Ten animals per group were inoculated by tail scarification two days after tumor implantation with 10 µl of crude lysate containing $1 \times 10^{10}$ pfu of wild type, V-WR or recombinant vaccinia virus, rV-CEA. The second and third virus inoculations were at 14 day intervals. Animals were checked weekly for the presence of tumors. Tumors were measured by caliper in two dimensions and the volume calculated using the formula: width$^2 \times$length+2.

Cyclophosphamide is an alkylating agent which is believed to moderate immune responses in tumor bearing animals and humans. Suppressor T-cells are known to be sensitive to this drug at concentrations that do not effect other subpopulations of lymphocytes. This drug can thus perhaps enhance host cellular immune recognition and responses against tumor cells. We demonstrate that immunomodulation of the hosts' immune system with cyclophosphamide given prior to vaccination can enhance the antitumor response to the immunizations.

Figure 10A:
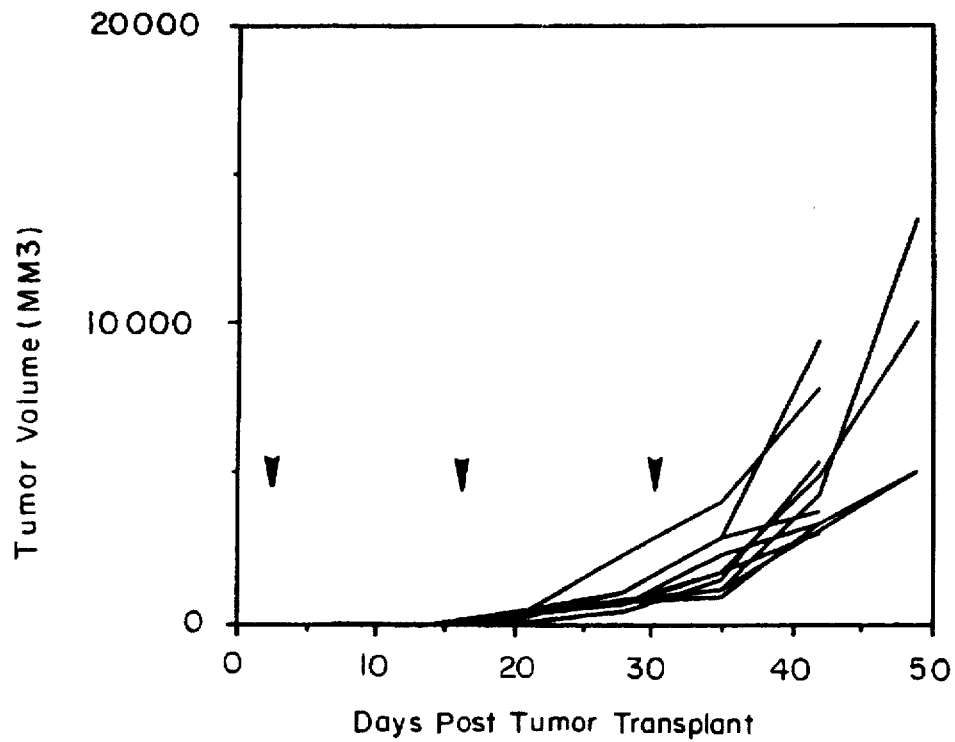
FIG. 10 shows the effect of administering cyclophosphamide in combination with the recombinant CEA vaccinia construct on the growth of a mouse adenocarcinoma cell line expressing human CEA. The C57/BL6 female mice were given cyclophosphamide (100 mg/kg) by intraperitoneal injection, two days prior to the implantation of the tumor. Two$\times 10^5$ MCA38 adenocarcinoma cells expressing human CEA were transplanted by subcutaneous injection and two days later the mice were administered by tail scarification either 10 µl of $1 \times 10^{10}$ pfu of wild type vaccinia (V-WR) or recombinant vaccinia (rV-CEA) followed by two additional inoculations 14 days apart. Subcutaneous tumors were measured in two dimensions, weekly, and the volumes calculated. Panel (A) shows the growth of tumor of 10 individual mice given cyclophosphamide and inoculated with wild type vaccinia (V-WR) virus. Panel (B) shows the growth of tumors of 10 individual mice inoculated with recombinant vaccinia (rV-CEA) virus containing human CEA. Arrows indicate days of vaccinia inoculations.
Figure 10B:
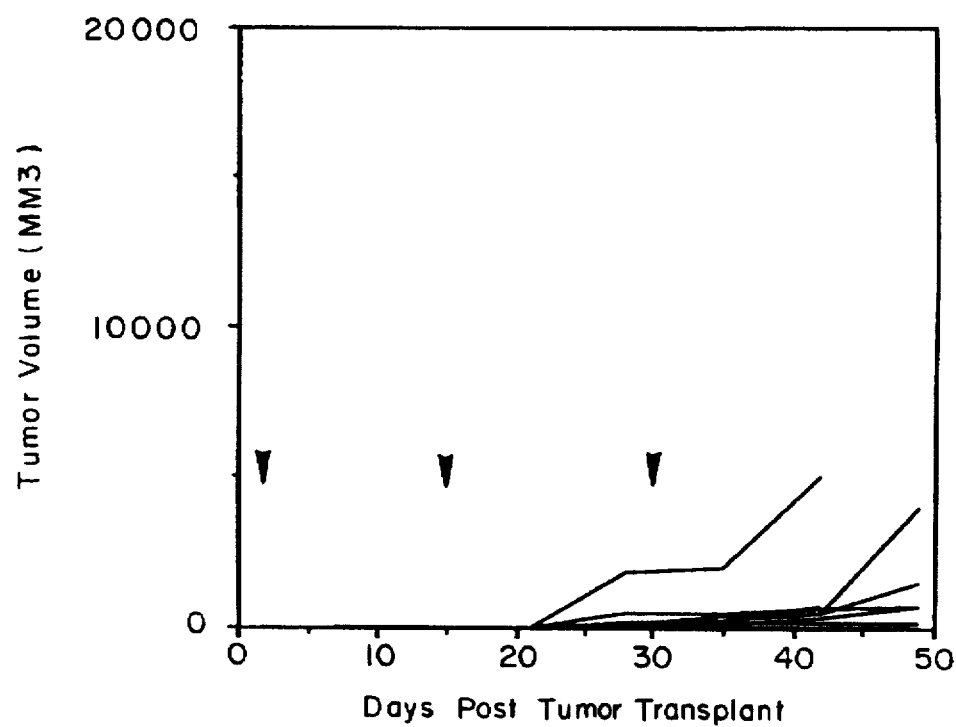

FIG. 10 shows the results of the growth of MCA38 human CEA expressing tumors in animals given cyclophosphamide and vaccinia immunizations. Ten individual animals were given 3 immunizations of either wild type vaccinia (V-WR; FIG. 10A) or recombinant (rV-CEA; FIG. 10B) after tumor implantation. Animals receiving cyclophosphamide and recombinant vaccinia (rV-CEA) showed a dramatic reduction in the size of the tumors over 49 days. Two animals failed to develop tumors. These animals have been rechallenged with $2 \times 10^5$ MCA38 murine adenocarcinoma cells expressing CEA and failed to develop tumors 120 days post challenge. In contrast, animals administered the wild type (V-WR) vaccinia and cyclophosphamide failed to stop tumor growth. Animals receiving no vaccinia, but cyclophosphamide also failed to inhibit tumor growth.

EXAMPLE 11

Therapy with vaccinia and human recombinant interleukin-2

Four to five week old female C57/BL6 mice obtained from the Frederick Cancer Research Facility were inoculated by subcutaneous injection with $2 \times 10^5$ MCA38 murine adenocarcinoma cells expressing human CEA. On days, +1, +2, 3 and +4 post tumor transplantation, the mice were administered 25,000 units of purified recombinant human interleukin-2 (rh IL-2; Cetus Corp.), $3.6 \times 10^6$ units/mg, twice a day by intraperitoneal injection. Also on day +2, animals were administered by tail scarification 10 µl of $1 \times 10^{10}$ pfu of either wild-type (V-WR) or the recombinant vaccinia (rV-CEA) virus. The next two immunizations were given 14 days apart. Animals were checked weekly for the presence of tumors. Tumors were measured by caliper in two dimensions and the volume calculated using the formula: width$^2$× length÷2.

Antitumor effects in both murine tumor models and in the treatment of human with metastatic cancer have sometimes been achieved using high doses of individual recombinant cytokines. For example, Rosenberg et al. (*N. Eng. J. Med.* 373:1485–1492, 1985) have achieved tumor regression using high doses of interleukin-2 alone or in combination with adoptive cellular therapy in mice and humans. Interleukin-2 is a protein released by activated helper T-lymphocytes. It is essential for the expansion of antigen triggered T-lymphocytes and cytotoxic T-cells which are frequently depressed in malignancy. The cytotoxic T-cells expanded by interleukin-2 (IL-2) are shown to retain antitumor activity in vivo.

Interleukin-2 also promotes the growth of natural killer (NK) cells and enhances murine natural killer cytotoxicity in vivo. Immunomodulation of the hosts' immune system with recombinant human interleukin-2 (rh IL-2) given prior to recombinant vaccination was demonstrated to enhance antitumor responses.

Figure 11A:
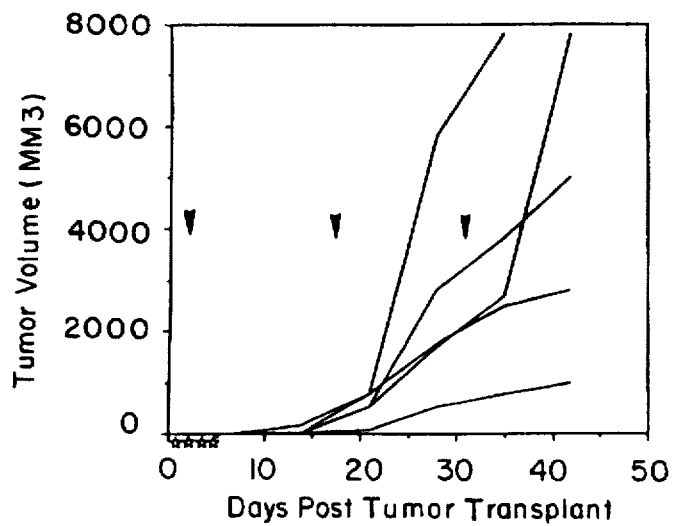
FIG. 11 shows the effect of administering recombinant human interleukin-2 (rh IL-2) and the recombinant CEA vaccinia construct on the growth of a murine adenocarcinoma cell line expressing human CEA. Five mice per group were transplanted with $2 \times 10^5$ MCA38 murine adenocarcinoma cells expressing human CEA. Recombinant human interleukin-2 (rh IL-2) was administered twice a day (25,000 units/injection) by intraperitoneal injection on days +1, +2, +3, +4 post tumor transplant. 10 µl of $1 \times 10^{10}$ pfu of either wild type vaccinia (V-WR) virus or recombinant vaccinia (rV-CEA) virus was administered by tail scarification on day +2. Two subsequent immunizations were given 14 days apart. The arrows indicate days of immunizations and the stars indicate days of recombinant human interleukin (rh IL-2) injections. Panel (A) shows tumor growth in animals receiving recombinant human interleukin-2 (rh IL-2) alone. Panel (B) shows tumor growth in animals administered rh IL-2 and wild-type vaccinia virus (V-WR) over 42 days. Panel (C) shows tumor growth in animals that had been administered rh IL-2 and recombinant vaccinia (rV-CEA) virus.
Figure 11B:
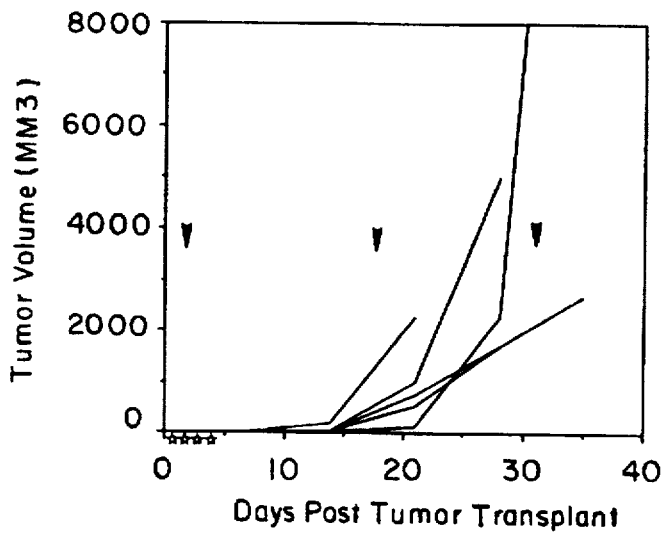
Figure 11C:
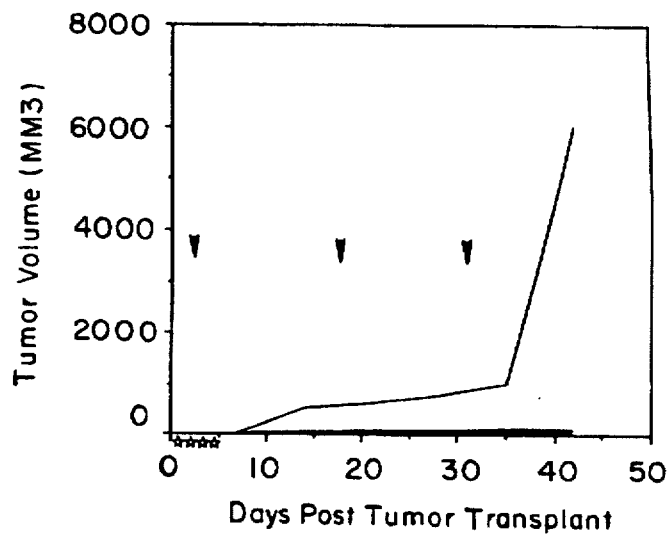

FIG. 11 shows the effect of the administration of recombinant human interleukin-2 (rh IL-2) and recombinant vaccinia virus (rV-CEA) on the growth of MCA38 murine adenocarcinoma cells expressing human CEA. Five animals per group were given recombinant human interleukin-2 (rh IL-2), alone (FIG. 11A), or recombinant human interleukin-2 plus subsequent immunizations of either wild type vaccinia virus (v-WR; FIG. 11B), or recombinant vaccinia (rV-CEA; FIG. 11C) by tail scarification 2 days after tumor transplantation. Animals receiving recombinant human interleukin-2 (rh IL-2) plus the recombinant vaccinia virus (rV-CEA) showed a dramatic reduction in tumor growth over the course of 42 days. In contrast, animals administered the recombinant human interleukin-2 (rh IL-2) plus wild type (V-WR) virus or recombinant human interleukin-2 (rh IL-2) alone developed rapidly growing tumors.

EXAMPLE 12

Construction and Testing of Recombinant Vaccinia-CEA Using New York City Strain of Vaccinia A recombinant CEA-vaccinia virus was produced using the New York City Board of Health strain of vaccinia virus obtained from ATCC (No. VR-325; Rockville). The recombinant virus, designated rV(NYC)-CEA, was produced by homologous recombination of the pSC-11 plasmid containing the human CEA gene as generally described in Example 1 above. The pSC-11 plasmid contained the *E. coli* Lac Z gene under the control of the vaccinia virus late promoter p-11. Use of this plasmid provided a selection method for obtaining recombinant viral particles. Expression of the rV(NYC)-CEA was detected by Western blot analysis using the MAb COL-1. Virus was grown in spinner cultures of HeLa cells, directly pelleted by centrifugation, and purified over a 20–40% sucrose gradient according to Mackett et al., *J. Virol.* 49:857–864 (1984), which is incorporated herein by reference.

The molecular weights of the CEA product expressed by the rV(NYC)-CEA and rV(WR)-CEA recombinant constructs were determined by Western blot analysis using the anti-CEAMAb COL-1. The 180-kilodalton product of purified human CEA and CEA detected in an extract of the established human colon carcinoma cell line GEO were used as controls. Extracts of cells infected with V-NYC, rV(NYC) -CEA, V-WR, and rV(WR)-CEA were also transferred to membranes and analyzed with COL-1. The rV(NYC)-CEA infected cells expressed a 90-kilodalton product, while the cells infected with wild-type V-NYC or V-WR showed no CEA present. Cells infected with the rV(WR)-CEA, on the other hand, expressed 90- and 180-kilodalton products that reacted with COL-1. The reasons for the variation in expression product are not presently known; however, Northern blot analysis of BS-C-1 cells infected with either rV(NYC) -CEA or rV(WR)-CEA detected mRNA species of 2.4 to 2.5 kb, indicating that the entire CEA transcript was present in these cells.

The more attenuated rV(NYC)-CEA construct was used to prevent the establishment of tumor transplants in an animal model. The MC-38 colon carcinoma cells with and without the transduced human CEA gene were used to determine if anti-tumor effects were directed against CEA. The wild-type V-NYC was also used as a control immunogen to ascertain that the protective immune responses generated were the consequence of the human CEA gene which had been inserted in the NYC vaccinia strain.

Figure 12A:
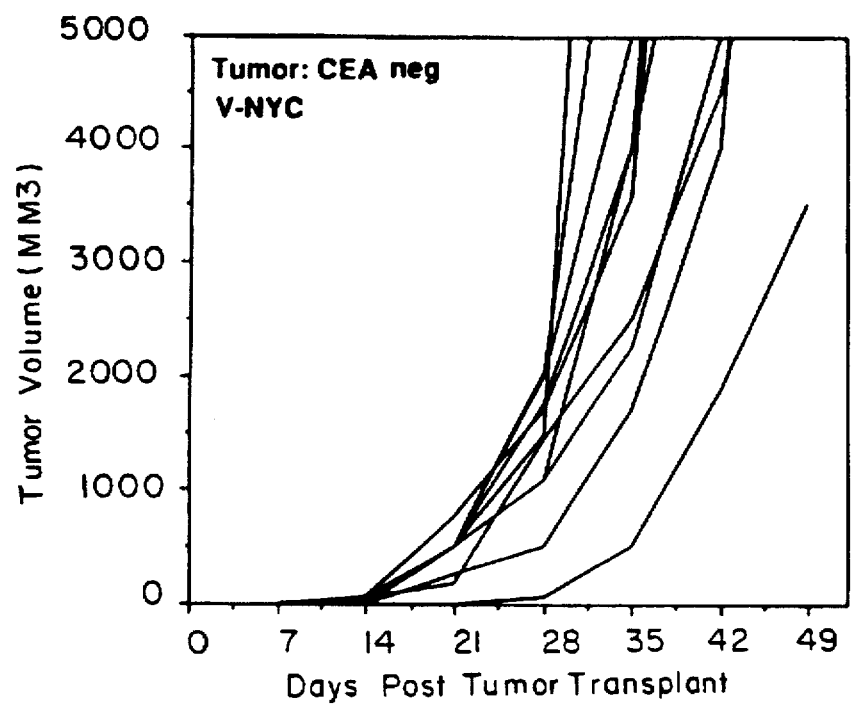
FIG. 12 illustrates the effect of prior vaccination with the recombinant CEA-vaccinia construct on the growth of a transplanted mouse adenocarcinoma cell line expressing human CEA. Ten mice per group were vaccinated by tail scarification with 10 µl of $10^7$ PFU of either V-NYC (panels A and C) or rV(NYC)-CEA (panels B and D). Three vaccinations were given 14 days apart. Seven days after the last vaccination (Day 0), $2 \times 10^5$ tumor cells were transplanted by subcutaneous inoculation. Panels A and B illustrate growth rates of the non-CEA expressing cell line MC-38, and panels C and D illustrate growth rate of the CEA-expressing tumors, MC-38-CEA-2. Weekly measurements were taken in two dimensions.
Figure 12B:
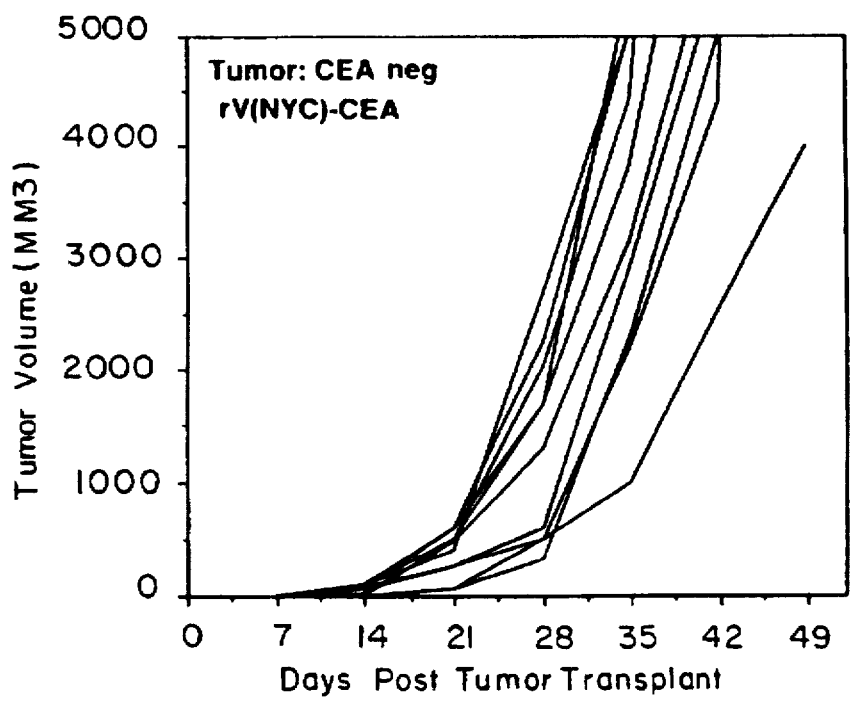

As shown in FIG. 12A and 12B, neither the wild-type nor recombinant vaccinia construct without the CEA insert conferred any protection against growth of transplanted non-CEA transduced tumor cells. Tumors from all 10 mice in each group grew rapidly at approximately the same rate. Non-transduced and CEA-transduced MC-38 tumors grew at similar rates in control animals receiving no vaccinia inoculation and at the same rate as tumors growing in mice which had received wild type vaccinia (V-NYC) inoculations.

Figure 12C:
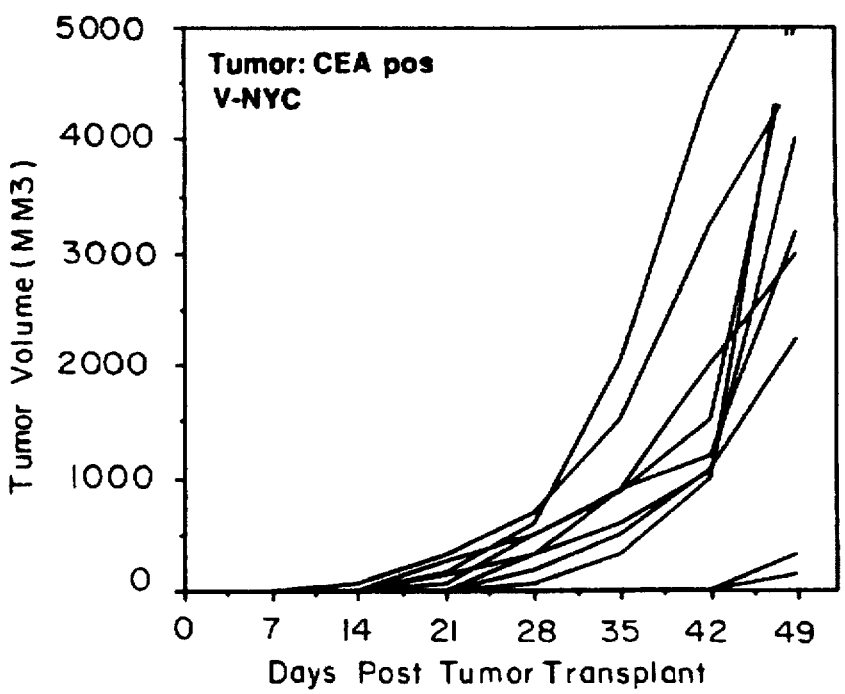
Figure 12D:
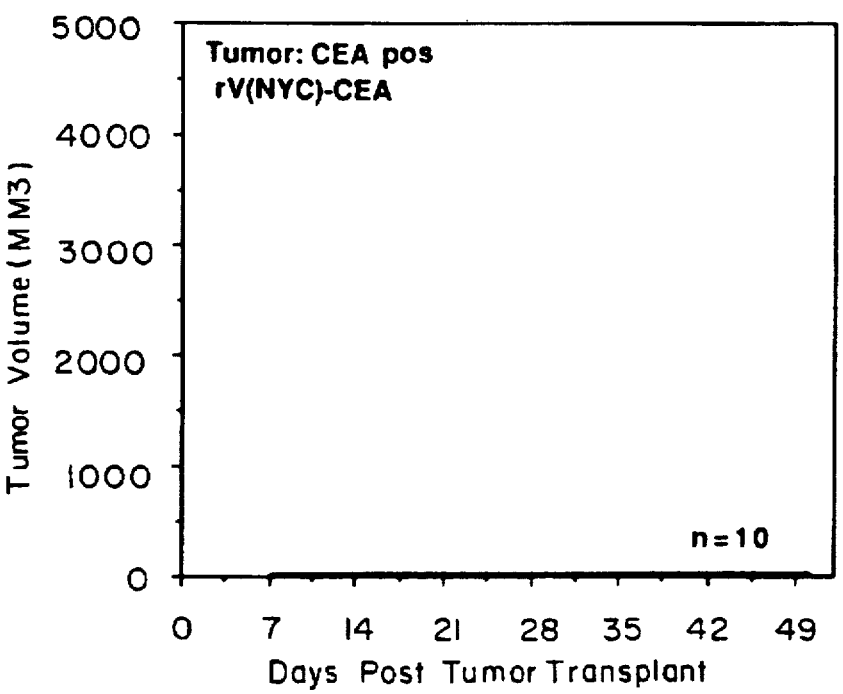

FIG. 12C and 12D compare the efficacy of the V-NYC versus the rV(NYC)-CEA in inhibiting the transplantation of the CEA-transduced colon carcinoma cells. As seen in FIG. 12C, in mice vaccinated with the wild-type V-NYC, 8/10 of transplanted tumors grew rapidly, and eventually all 10 tumors grew. In contrast, no tumors grew in any of the 10 mice vaccinated with the rV(NYC)-CEA construct. Furthermore, these mice immunized with rV(NYC)-CEA remained tumor free for 120 days following their first tumor challenge; at day 120 they were challenged with 1×10$^6$ CEA-transduced tumor cells and again remained tumor free throughout an additional 120 day observation period. No toxicity due to the administration of rV(NYC)-CEA or V-NYC was observed.

Figure 13A:
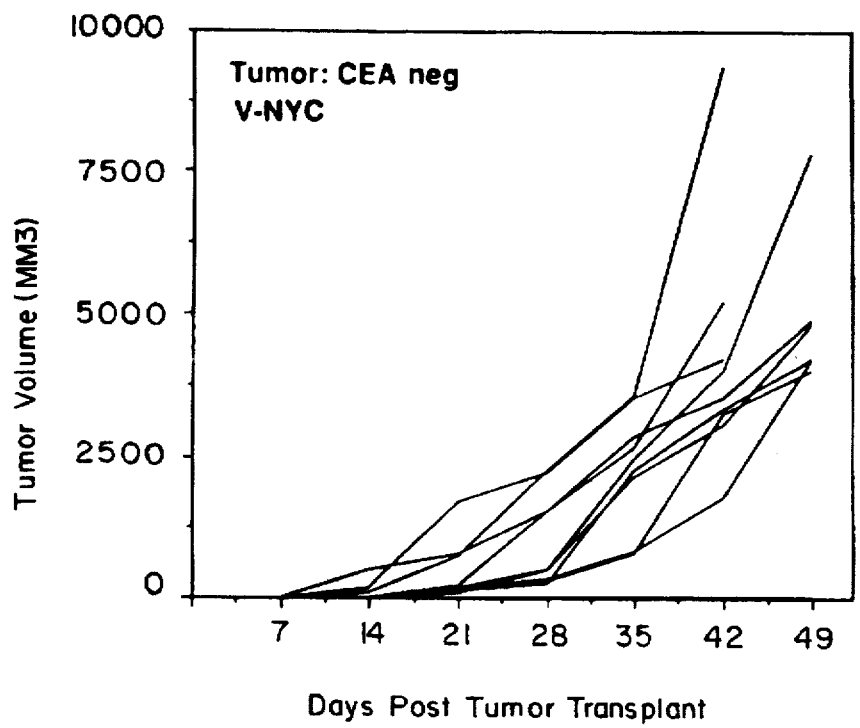
FIG. 13 illustrates the treatment of mice bearing CEA transduced and untransduced MC-38 mouse colon adenocarcinomas with rV(NYC)-CEA. Ten mice per group were injected subcutaneously with $2 \times 10^5$ MC-38 cells (panels A and B) or the CEA transduced MC-38-CEA-2 cells (panels C and D) at Day 0. Seven days later, the animals were vaccinated by tail scarification with 10 µl of $10^7$ PFU of either V-NYC (panels A and C) or rV(NYC)-CEA (panels B and D). Two more vaccinations were given 14 days apart at days 21 and 35. Tumors were measured weekly in 2 dimensions.
Figure 13B:
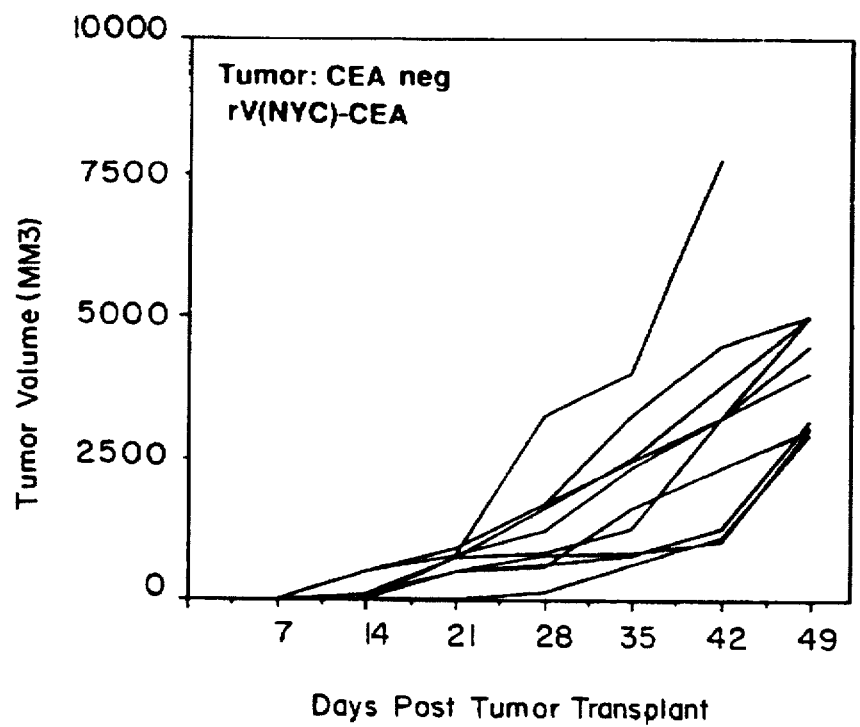
Figure 13C:
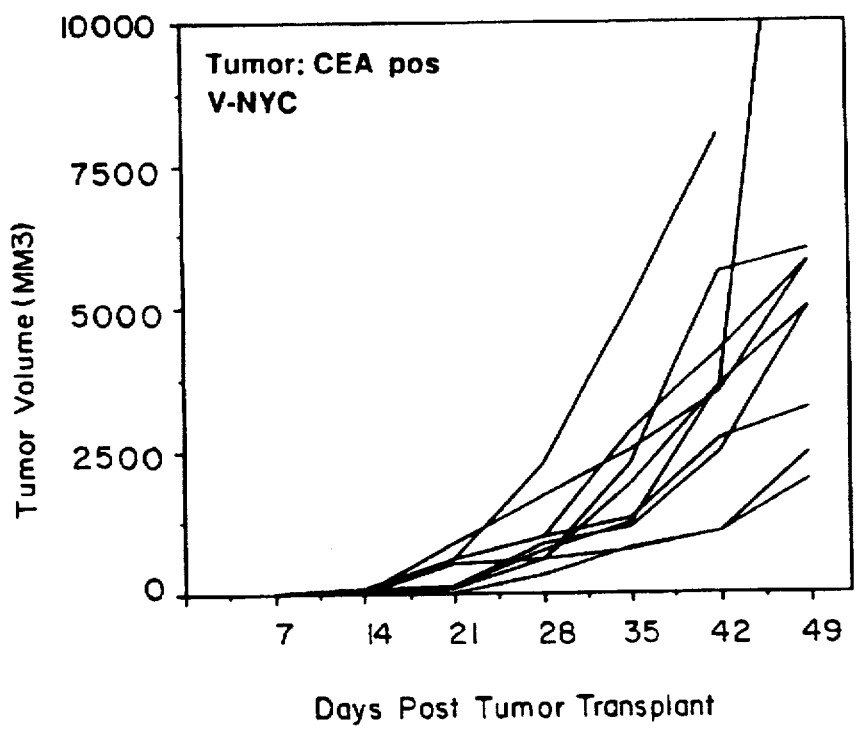
Figure 13D:
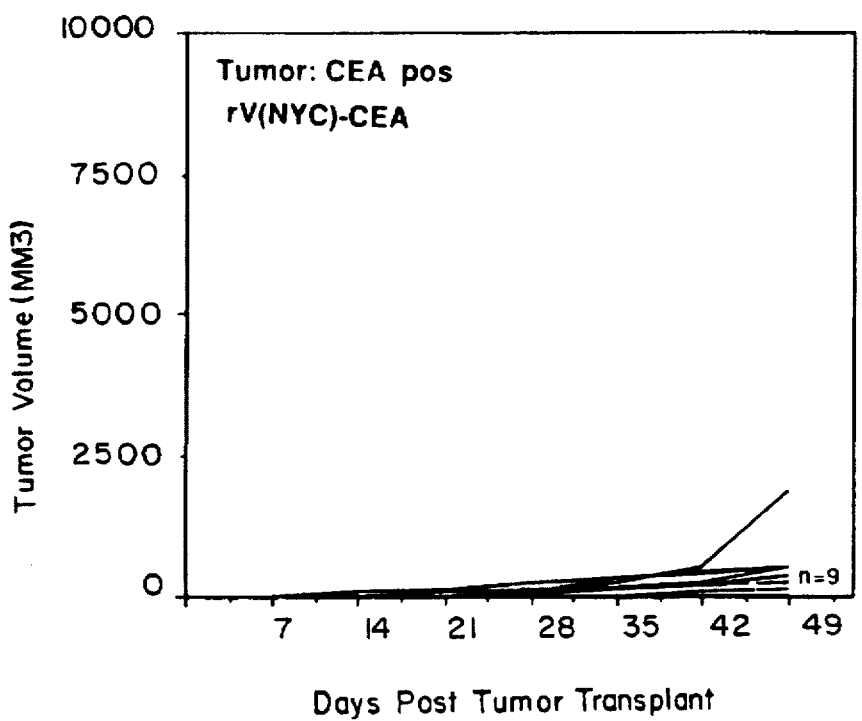

Vaccination with the rV(NYC)-CEA construct was also shown to be effective in tumor treatment, i.e., to inhibit the growth of established tumors. Tumors were transplanted into animals seven days prior to recombinant vaccinia virus treatment. As seen in FIG. 13A and 13B, the growth rates of the MC-38 carcinoma cells (non-CEA-transduced) were similar regardless of whether the V-NYC or rV(NYC)-CEA constructs were used for treatment. Similar tumor growth rates were also seen in mice bearing the CEA-transduced MC-38 cells when treated with the wild type V-NYC (FIG. 13C). In contrast, however, greatly reduced tumor growth was seen in all 10 tumor bearing mice treated with the rV(NYC)-CEA construct (FIG. 13D). Moreover, three animals in this group that failed to develop tumors for four months were again challenged with 1×10$^6$ CEA-transduced MC-38 cells and remained tumor free through an additional 120 day observation period. Non CEA-transduced MC-38 tumors implanted at the same time on the contralateral side grew at the site. No toxicity due to the administration of the rV(NYC)-CEA was observed in the treated animals.

The nature of the immune response elicited by the rV(NYC)-CEA vaccinia vaccine was examined. As seen in Table 2, sera titers to CEA ranged from 1:700 to 1:5,250 (average, 1:2,255) in mice administered rV(NYC)-CEA, with titers at or below 1:20 (average ≦1:82) observed in all 14 mice inoculated with V-NYC and in all 24 pre-inoculation sera. All sera in the pre-inoculation groups and in groups inoculated with either vaccinia construct were also negative or weakly positive for reactivity to ovalbumin, with the exception of one mouse with a titer of 1:750. The dynamics of increase in antibody titer following inoculation with rV(NYC)-CEA was also monitored. Following the first inoculation, there was a modest rise in anti-CEA titer, which greatly increased after the second and third inoculations with rV(NYC)-CEA.

TABLE 2

Reactivity of Sera Derived from rV(NYC)-CEA and V-NYC Inoculated Mice Against Purified CEA and Ovalbumin

| Immunogen | Mouse | Titer to CEA (OD = .5) Pre | D35 | Titer to Ovalbumin (OD = .5) Pre | D35 |
|---|---|---|---|---|---|
| V-NYC | 1 | <50 | 50 | <50 | 50 |
| | 2 | <50 | 150 | <50 | <50 |
| | 3 | <50 | 150 | <50 | 90 |
| | 4 | <50 | 150 | <50 | 100 |
| | 5 | <50 | 200 | <50 | 100 |
| | 6 | <50 | <50 | <50 | <50 |
| | 7 | <50 | <50 | <50 | <50 |
| | 8 | <50 | <50 | <50 | <50 |
| | 9 | <50 | <50 | <50 | <50 |
| | 10 | <50 | <50 | <50 | <50 |
| | 11 | <50 | <50 | <50 | <50 |
| | 12 | <50 | <50 | <50 | <50 |
| | 13 | <50 | <50 | <50 | <50 |
| | 14 | <50 | <50 | <50 | <50 |
| rV(NYC)-CEA | 1 | <50 | 2500 | <50 | 100 |
| | 2 | <50 | 5250 | <50 | 70 |
| | 3 | <50 | 3250 | <50 | 125 |
| | 4 | <50 | 1750 | <50 | 200 |
| | 5 | <50 | 3900 | <50 | 200 |
| | 6 | <50 | 1200 | <50 | 250 |
| | 7 | <50 | 1900 | <50 | 750 |
| | 8 | <50 | 850 | <50 | 175 |
| | 9 | <50 | 1250 | <50 | 250 |
| | 10 | <50 | 700 | <50 | 200 |

Humoral Response of Mice Inoculated with rV(NYC)-CEA and wild type rV-NYC. C57BL/6 mice were inoculated three times by tail scarification with $10^7$ PFU of purified rV(NYC)-CEA or V-NYC. Starting at 1:50, five-fold dilutions of sera taken prior to immunization (designated pre) and day 35 post immunization were tested by ELISA for reactivity to purified CEA and control antigen, ovalbumin. Individual serum titers were determined as the dilution factor at an optical density (A490) of 0.5.

Cell mediated immune responses to the rV(NYC)-CEA construct were measured using assays for delayed-type hypersensitivity (DTH), lymphoproliferation and cytotoxicity. DTH reactions were determined in mice inoculated with either 2 or 3 times with rV(NYC)-CEA or V-NYC by tail scarification (10 µl of $10^7$ PFU, given 14 days apart. Six days after the last vaccinia inoculation, one footpad was injected with irradiated non-transduced MC-38 cells (20 µl of $5\times10^5$ MC-38 cells in PBS) and the other with the irradiated CEA-transduced MC-38 cells ($5\times10^5$ MC-38-CEA-2 cells in PBS). The thickness of footpads was measured 48 h after challenge.

Little or no differences between footpads were noted in mice injected with control PBS solution, which were then used to determine baseline values. Similar negative results were obtained when mice were inoculated two times with the V-NYC construct. Two of ten mice injected 2 times with rV(NYC)-CEA showed some differential swelling in the footpad injected with the CEA-transduced tumor cells. Mice injected 3 times with the V-NYC construct showed little or no DTH response to the CEA-transduced tumors, while the majority of mice (14/20) injected 3 times with the rV(NYC)-CEA construct demonstrated a differential DTH reactivity to the CEA-transduced tumor cells. The difference in DTH results following three injections of rV(NYC)-CEA versus the V-NYC construct was statistically significant (p<0.001, Student's t test). Thus, the results demonstrated that three administrations of rV(NYC)-CEA were apparently superior to two administrations (p values of <0.001 vs. <0.01) in eliciting a DTH reaction to human CEA transduced tumor cells.

To assess lymphoproliferative response as a result of vaccination with rV(NYC)-CEA, splenic T cells isolated from unimmunized or immunized mice 28 days after the third and final vaccinia challenge were examined for functional competence and antigen specificity indicated by proliferation in response to various stimuli (Table 3). Of the three groups of T-lymphocytes tested, only those from mice immunized with rV(NYC)-CEA responded to soluble CEA. Antigen specificity to CEA was revealed using ovalbumin, an irrelevant soluble antigen, which failed to stimulate lymphocytes from these mice. In addition to CEA, lymphocytes from rV(NYC)-CEA mice responded to UV-inactivated vaccinia virus on recall challenge in vitro. Furthermore, lymphocytes from mice receiving V-NYC, but not unimmunized mice, demonstrated reactivity to UV-inactivated vaccinia virus, thus confirming specificity to this viral antigen and functional competence of the V-NYC group. Finally, all three groups of lymphocytes responded strongly to Con A as a general measure of functional T cell competence. Thus, immunization with rV(NYC)-CEA, but not V-NYC, induced T cell responsiveness to CEA, which correlated with an anti-tumor effect in vivo.

TABLE 3

Lymphoproliferative Responses of Mice Immunized With V-NYC or rV(NYC)-CEA

| Immunogen[1] | $^3$H-Thymidine Incorporation (cpm)[2] | | | | |
|---|---|---|---|---|---|
| | Media | ConA | Vaccinia | CEA | Ovalbumin |
| rV(NYC)-CEA | 2,679 ±309 | 153,247 ±8079 | 41,982 ±3683 | 51,963 ±1726 | 2,502 ±186 |
| V-NYC | 2,319 ±270 | 132,443 ±5274 | 40,206 ±2924 | 3,275 ±205 | 2,725 ±391 |
| None | 747 ±72 | 126,120 ±6778 | 539 ±132 | 385 ±44 | 486 ±115 |

[1]C57BL/6 mice were inoculated with $1 \times 10^7$ PFU of V-NYC or rV-NYC-CEA by tail scarification on three separate occasions separated 14 days apart. Splenic T cells were then purified from such mice 28 days after the final exposure. Unimmunized mice, which received nothing, served as an additional control.
[2]Lymphocytes ($1 \times 10^5$/well) were incubated in the presence of irradiated, normal syngeneic splenocytes ($5 \times 10^5$/well) without (media control) and with various stimuli: Con A (2 µg/ml), UV-inactivated V-NYC ($1 \times 10^7$ PFU/ml), purified CEA (50 µg/ml; from Vitro Diagnostics) or purified ovalbumin (50 µg/ml), for up to 3 (Con A) or 5 (for antigens) days. Cultures were pulsed with [$^3$H]-thymidine ($^1$ µCi/well) for the final 18–24 hr of their incubation period and incorporated radioactivity determined by liquid scintillation spectroscopy. Data are reported as the mean cpm ± SEM of triplicate wells.

To assess the presence of a vaccine-induced anti-CEA cytotoxicity response in the animals, splenic T lymphocytes were isolated directly from V-NYC or rV(NYC)-CEA immunized mice 5 days after a second vaccinia challenge.

since CTL induction would be maximal shortly after a boost. The results, shown in Table 4, indicate that lymphocytes from mice immunized with rV(NYC)-CEA, but not V-NYC, mediated lysis of MC-38-CEA-2 tumor cells which bear the cognate antigen. In contrast, under similar incubation conditions with both effector groups, only background levels of lytic activity were detectable against MC-38, the CEA-negative tumor target. In the presence of Con A, which circumvents antigen-specific recognition and facilitates lectin-dependent cellular cytotoxicity, both effector groups efficiently lysed MC-38, confirming that lymphocytes from mice receiving V-NYC were lytically active and that the tumor cell line was not intrinsically resistant to lysis.

TABLE 4

Cytotoxic Lymphocyte-Mediated Lysis Against CEA-Expressing Tumors

| | | % Specific Release[3] | | | |
|---|---|---|---|---|---|
| | | MC-38-CEA-2 | | MC-38 | |
| Effectors[1] | Con A[2] | 40:1[4] | 20:1 | 40:1 | 20:1 |
| rV(NYC)-CEA | − | 36 ± 3 | 22 ± 5 | 14 ± 3 | 7 ± 2 |
| | + | NT | NT | 55 ± 4 | 38 ± 2 |
| V-NYC | − | 12 ± 3 | 6 ± 2 | 10 ± 2 | 6 ± 1 |
| | + | NT | NT | 55 ± 5 | 40 ± 4 |

[1]C57BL/6 mice were inoculated with 1 × 10[7] PFU of V-NYC or rV(NYC)-CEA by tail scarification on two separate occasions separated 14 days apart. Splenic T cells were then purified from such mice 5 days after the final exposure.
[2]Con A (2.5 μg/ml) was added directly to the indicated cultures to induce lectin-dependent cellular cytotoxicity.
[3]Lytic activity was assessed against CEA-transduced (MC-38-CEA-2) and non-transduced (MC-38) targets in a conventional $^{51}$Cr-release assay at two effector:target ratios. Reactions were terminated after 16 hr and the % specific lysis determined and reported as the mean ± SEM of triplicate cultures. Similar lytic patterns were observed in a 4 hr assay, although overall the activities were lower. NT, not tested.
[4]Effector to target cell ratios were 40:1 and 20:1.

Certain types of anti-idiotype MAbs can be considered as surrogate immunogens because they may mimic the antigenic specificity of the original antigen. Certain anti-idiotype MAbs can be used as immunogens, presenting an epitope in a unique way, to enhance a host's immune response to the original antigen.

In this instance, a series of MAbs (Abls) have been made that are reactive with CEA. See, Muraro et al., Cancer Res. 45:5769–5780 (1985) and Herlyn et al., Hybridoma 2:329–339 (1983), and Kuroki et al., Int. J. Cancer 44:208–218 (1989), which are incorporated herein by reference. One of these MAbs is termed COL-1. COL-i, a murine IgG, was used as an immunogen to prepare a series of Ab2 MAbs, or anti-idiotype MAbs. The anti-idiotype MAbs were selected for their ability to block the binding of MAb COL-1 to CEA. One of these anti-idiotype MAbs was selected for further study and has been designated CAI-5.

Studies were performed in which the anti-id CAI-5 was used as a boost to vaccination with rV(NYC)-CEA. Challenge of the immunized animals with CEA-transduced tumor cells indicated a strong synergy effect may be provided in the prophylaxis and treatment of CEA-bearing tumors by use of anti-id Abs in conjunction with an initial immunization with a CEA recombinant vector. C57BL/6 mice were inoculated one time with 1×10[7] PFU of V(NYC) wild type vaccine or rV(NYC)-CEA recombinant vaccine. Two week later, mice received an immunization of either PBS alone or 100 μg/100 μl of anti-idiotype MAb CAI-5 emulsified in incomplete Freund's adjuvant. Seven days following the boost, the mice received a subcutaneous inoculation of CEA transduced tumor cells. Tumor growth was measured 21 days following the challenge of tumor cells.

The results showed that 4 of 4 mice receiving a single injection of control vaccine, V-NYC, and boosted with PBS, developed tumors. Five of 5 mice receiving V-NYC and boosted with anti-idiotype MAb CAI-5 also developed tumors. Three of 5 mice receiving one injection of rV(NYC)-CEA and a PBS boost developed tumors (ave. tumor volume - 388mm[3]). However, none of 5 mice receiving one injection of rV(NYC)-CEA and boosted with anti-idiotype MAb CAI-5 had tumors. These studies demonstrate that the use of an anti-idiotype MAb following immunization with a recombinant vaccinia vaccine may be a preferred mode of immunization.

EXAMPLE 13

Immunogenicity and Safety of rV(NYC)-CEA Vaccine in Primates

Studies were conducted to determine the immune response elicited by rV(NYC)-CEA vaccine in primates, as well as to assess the safety of such a vaccine.

Twelve adult male rhesus monkeys (Macaca mulatta), ages 5 to 7 years, were used. The monkeys were immunized either 3 or 4 times at 6 week intervals by skin scarification with 10 μl or 50 μl of purified virus containing 1×10[8] or 5×10[8] plaque forming units (PFU) of either rV(NYC)-CEA or V-NYC. Four animals received 1×10[8] PFU of rV(NYC)-CEA, 4 animals received 5×10[8] PFU rV(NYC)-CEA, and 4 animals received 5×10[8] PFU V-NYC. The immunization protocol is set forth in detail in Table 5.

TABLE 5

Inoculation Protocol of Rhesus Monkeys with the CEA Recombinant and Wild Type Vaccinia Virus

| Experiment | Monkey Number | Immunogen | Dose[a,b] | Boosts[c] |
|---|---|---|---|---|
| I. | 1 | V-NYC | 5 × 10[8] | 42, 84, 174 |
| | 2 | V-NYC | 5 × 10[8] | 42, 84, 174 |
| | 3 | rV-(NYC)-CEA | 5 × 10[8] | 42, 84, 174 |
| | 4 | rV-(NYC)-CEA | 5 × 10[8] | 42, 84, 174 |
| | 5 | rV-(NYC)-CEA | 1 × 10[8] | 42, 84, 174 |
| | 6 | rV-(NYC)-CEA | 1 × 10[8] | 42, 84, 174 |
| II. | 7 | V-NYC | 5 × 10[8] | 42, 84 |
| | 8 | V-NYC | 5 × 10[8] | 42, 84 |
| | 9 | rV(NYC)-CEA | 5 × 10[8] | 42, 84 |
| | 10 | rV(NYC)-CEA | 1 × 10[8] | 42, 84 |
| | 11 | rV(NYC)-CEA | 1 × 10[8] | 42, 84 |
| | 12 | rV(NYC)-CEA | 1 × 10[8] | 42, 84 |

[a]dermal route doses at 6 week intervals
[b]group I received 4 doses of immunogen
[c]days post first inoculation (Day 1)

Safety: The area of the lesions induced by the vaccines were analyzed 24 hours following each inoculation. In general, more swelling was seen after the first two inoculations as compared to the third or fourth inoculation. The duration of the lesions following each immunization, however, was approximately the same. Regional lymph node swelling following vaccination was greater in some monkeys following the first immunization as compared to the second, third or fourth immunizations. In general, no differences were seen in the parameters with the use of the rV(NYC)-CEA or the V-NYC vaccines.

Monkeys receiving the wild type vaccinia virus were compared to the monkeys receiving the recombinant vaccinia virus with respect to temperature, weight, regional lymphadenopathy, and the presence of splenomegaly and hepatomegaly. Mild temperature elevations were seen in all animals following vaccination. A mild regional lymphadenopathy was observed for several weeks following the immunizations, but there was no evidence of weight loss, hepatomegaly or splenomegaly in any of the animals, and no differences between control and recombinant vaccinated animals. Animals were tested for complete blood count, differential, hepatic (serum albumin, bilirubin, SGOT, SGPT, and gamma glutamyl transpeptidase) and renal chemistries (blood urea nitrogen and serum creatinine levels), all of which remained normal in all animals throughout the study period, or no significant differences were observable between recombinant vaccinated and wild type vaccinated animals.

Monkey (and human) granulocytes were evaluated for expression of non-specific cross-reacting antigen (NCA) and CEA. The CEA gene has been shown to belong to the immunoglobulin gene superfamily and has been shown to share some homology with proteins expressed on some normal adult tissues, such as NCA found on normal human granulocytes. CEA has not been previously shown to be expressed on human granulocytes. The possibility of inducing an immunological cross-reactivity to NCA was assessed by differential blood count and ELISA. There was no difference in differential counts in any of the vaccinated animals, and no anti-NCA responses were induced by vaccination with rV(NYC)-CEA. Surface NCA expression on monkey granulocytes was determined by flow cytometry using monoclonal antibodies B6.2 (which has previously been shown to react with human NCA; Horan Hand et al., *Int. J. Biol. Markers* 7:1–15 (1992)) and B1.1 (previously shown to react with an epitope shared by NCA and CEA; Kuroki et al., *Int. J. Cancer* 44:208–218 (1989)). Both antibodies showed significant surface reactivity to NCA on the surface of the monkey granulocytes. Immunization of the animals with a recombinant vaccinia virus expressing CEA did not elicit any apparent immune responses against NCA epitopes.

Immunogenicity: Immunized monkeys were tested for both humoral and cellular immune responses induced by rV(NYC)-CEA.

Sera from each of the monkeys were analyzed in ELISA for immunoreactivity to CEA, NCA and ovalbumin (OVA) as a control antigen. Anti-CEA antibody was quantitated by ELISA using microtiter plates coated with 100 ng of purified CEA, NCA (purified from crude perchloric acid extracts of normal human lung according to Koroki et al., *Cancer Res.* 211:713–720 (1981)), or ovalbumin (Sigma, St. Louis) in PBS. The plates were blocked with 5% BSA in PBS, dried and stored at −20° C. until used. The plates were incubated with various dilutions of monkey sera as well as MAb COL-1 as a standard control for 1 hr at 37° C. Plates were washed and antibody detected with horseradish peroxidase conjugated goat anti-human IgG Fc specific antisera (1:8000; Southern Biotechnology, Inc., Birmingham, Ala.) followed by a 10 min incubation with 100 μl of 2.8 mM o-phenylenediamine dihydrochloride in 0.015% hydrogen peroxide in 0.17 phosphate-citrate buffer, pH 5.0. The reactions were stopped by the addition of 25 μl of 4N sulfuric acid and the absorbance read at 490 nm using a Bio-Tek microplate ELISA reader.

Figure 14:
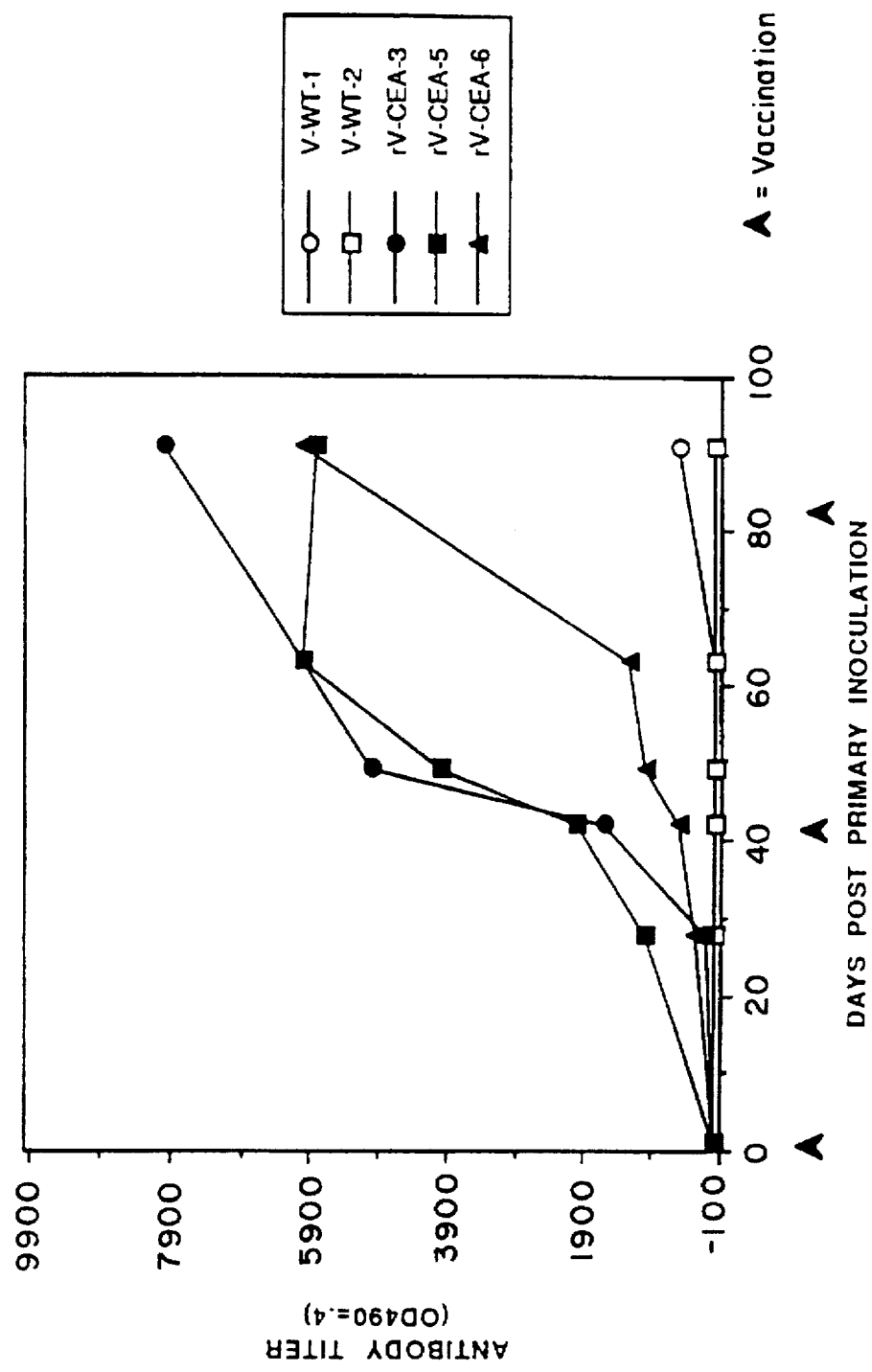
FIG. 14 illustrates antibody responses to inoculation with recombinant vaccinia virus in monkeys. Animals were vaccinated on days 1, 42, 84 (arrows) with either V-NYC (open symbols) or rV(NYC)-CEA (closed symbols). Anti-CEA antibody was quantitated at different time points by ELISA.

The results, shown in Table 6, indicate that all preimmune sera were negative against all three antigens. At Day 28 following primary immunization, strong antibody titers (greater than 1:1,000 serum dilution) were observed to CEA in two of the eight rV(NYC)-CEA inoculated monkeys. At Day 49, one week following the first boost, antibody titers at or greater than a 1:250 serum dilution were seen in all eight monkeys receiving the rV(NYC)-CEA and in none of the monkeys receiving the V-NYC. Similar results were seen at Day 63. At Day 91 (seven days following the second boost) antibody titers of greater than 1:1,000 serum dilution were seen in all seven monkeys tested that received the rV(NYC)-CEA, with titers of greater than or equal to 1:5,800 in four monkeys. An immune response to NCA of 1:1250 was observed in one of the eight monkeys receiving the rV(NYC)-CEA at Day 91, but some reactivity to OVA was also seen in this monkey. Two other monkeys, one receiving V-NYC and one receiving rV(NYC)-CEA, also showed some antibody titer to NCA at Day 91; however, identical titers were also seen to OVA, suggesting a potential nonspecific reactivity. It thus appears that the rV(NYC)-CEA induced a strong response for epitopes expressed on CEA in rhesus monkeys with little or no responses to NCA specific epitopes. The temporal nature of the anti-CEA response is depicted in FIG. 14.

TABLE 6

Primate Antibody Response to inoculation with Recombinant Vaccinia Virus[a]

| Monkey Immunogen Number | Preimmune Sera | | | Day 28 | | | Day 49 | | | Day 63 | | | Day 91 | | |
|---|---|---|---|---|---|---|---|---|---|---|---|---|---|---|---|
| | CEA | NCA | OVA | CEA | NCA | OVA | CEA | NCA | OVA | CEA | NCA | OVA | CEA | NCA | OVA |
| 1 V-NYC | ND[b] | ND | ND | ND | ND | ND | ND | ND | ND | ND | ND | ND | 500 | 400 | 500 |
| 2 V-NYC | ND | ND | ND | ND | ND | ND | ND | ND | ND | ND | ND | ND | ND | ND | ND |
| 3 rV(NYC)-CEA | ND | ND | ND | 100 | ND | ND | 5000 | 60 | ND | 6000 | ND | ND | 8000 | 500 | 500 |
| 4 rV(NYC)-CEA | ND | ND | ND | 4000 | ND | ND | 5000 | ND | ND | 6000 | ND | ND | 6000 | ND | ND |
| 5 rV(NYC)-CEA | ND | ND | ND | 1000 | ND | ND | 2000 | ND | ND | 6000 | 50 | ND | 5800 | 1250 | 250 |
| 6 rV(NYC)-CEA | ND | ND | ND | 250 | ND | ND | 1000 | ND | ND | 1250 | ND | ND | 6000 | ND | ND |
| | Preimmune Sera | | | Day 28 | | | Day 49 | | | Day 56 | | | Day 84 | | |
| 7 V-NYC | ND | ND | ND | ND | ND | ND | ND | ND | ND | ND | ND | ND | ND | ND | ND |
| 8 V-NYC | ND | ND | ND | 50 | ND | ND | ND | ND | ND | ND | ND | ND | ND | ND | ND |
| 9 rV(NYC)-CEA | ND | ND | ND | NT[c] | ND | ND | 1250 | ND | ND | 1000 | ND | ND | NT | NT | NT |
| 10 rV(NYC)-CEA | ND | ND | ND | 50 | ND | ND | 400 | ND | ND | 600 | ND | ND | 2000 | ND | ND |
| 11 rV(NYC)-CEA | ND | ND | ND | 50 | ND | ND | 600 | ND | ND | 500 | 50 | ND | 1000 | ND | ND |
| 12 rV(NYC)-CEA | ND | ND | ND | ND | ND | ND | 250 | ND | ND | 250 | ND | ND | 1000 | ND | ND |

TABLE 6-continued

| Primate Antibody Response to inoculation with Recombinant Vaccinia Virus[a] |||||||||||||||
|---|---|---|---|---|---|---|---|---|---|---|---|---|---|---|
| Monkey Immunogen Number | CEA | NCA | OVA | CEA | NCA | OVA | CEA | NCA | OVA | CEA | NCA | OVA | CEA | NCA | OVA |

[a]Monkeys received vaccinations of days 1, 42, 84. Sera was tested via ELISA.
[b]ND = Not Detectable, limit of detection was 1:50 dilution.
[c]NT = Not tested.

A serum sample from one monkey 35 days following initial vaccination with rV-CEA was analyzed by Western blot for reactivity to CEA, NCA and ovalbumin. The antiserum was shown in the blots to recognize purified CEA, but not ovalbumin or purified NCA. Preimmunization sera derived from the same monkey did not detect CEA, NCA or ovalbumin. Monoclonal antibodies COL-1 and B6.2 that recognize CEA and NCA, respectively, were used as positive controls.

Figure 15A:
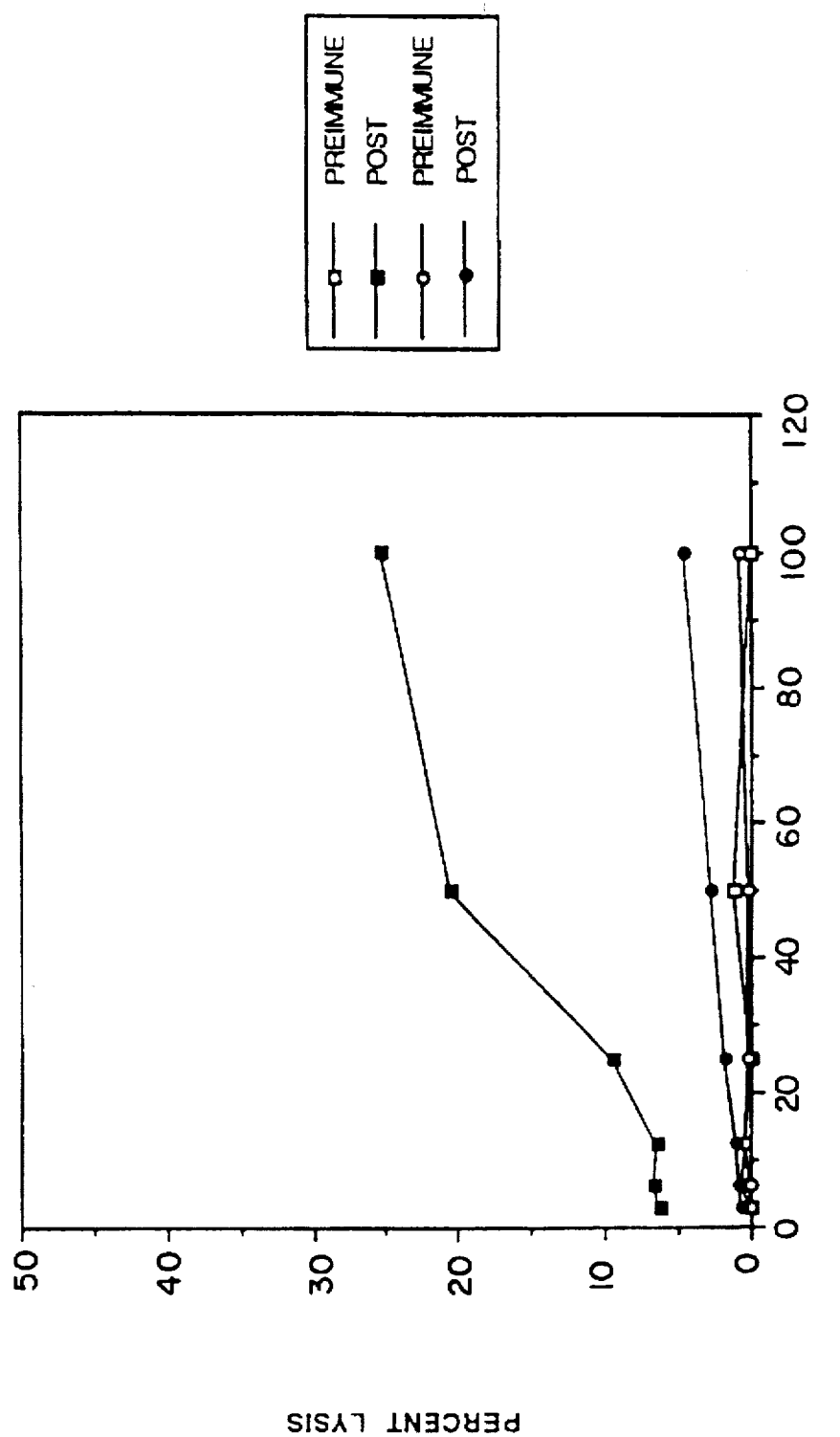
FIG. 15 illustrates the specificity of ADCC activity of human PBMC by rV-CEA induced monkey antisera. (A) Sera obtained from monkeys inoculated 2 times with rV-CEA were tested in an ADCC assay for activity against murine tumor cells expressing the CEA protein. Prior to the addition of human PBMCs, the target cells ($1 \times 10^4$) were preincubated for one hour at 37° C. with a 1:50 dilution of preimmunization sera (open symbols) or sera obtained 21 days following the second immunization (closed symbols). Sera was tested for ADCC activity against a murine colon carcinoma cell line transfected with CEA (squares) or the non-transduced control tumor cells (circles). (B) Same as A, except that human effector cells were pretreated with for 18 h with IL-2 (100 U/ml). Sera was tested for ADCC activity against a murine colon carcinoma cell line transfected with CEA.
Figure 15B:
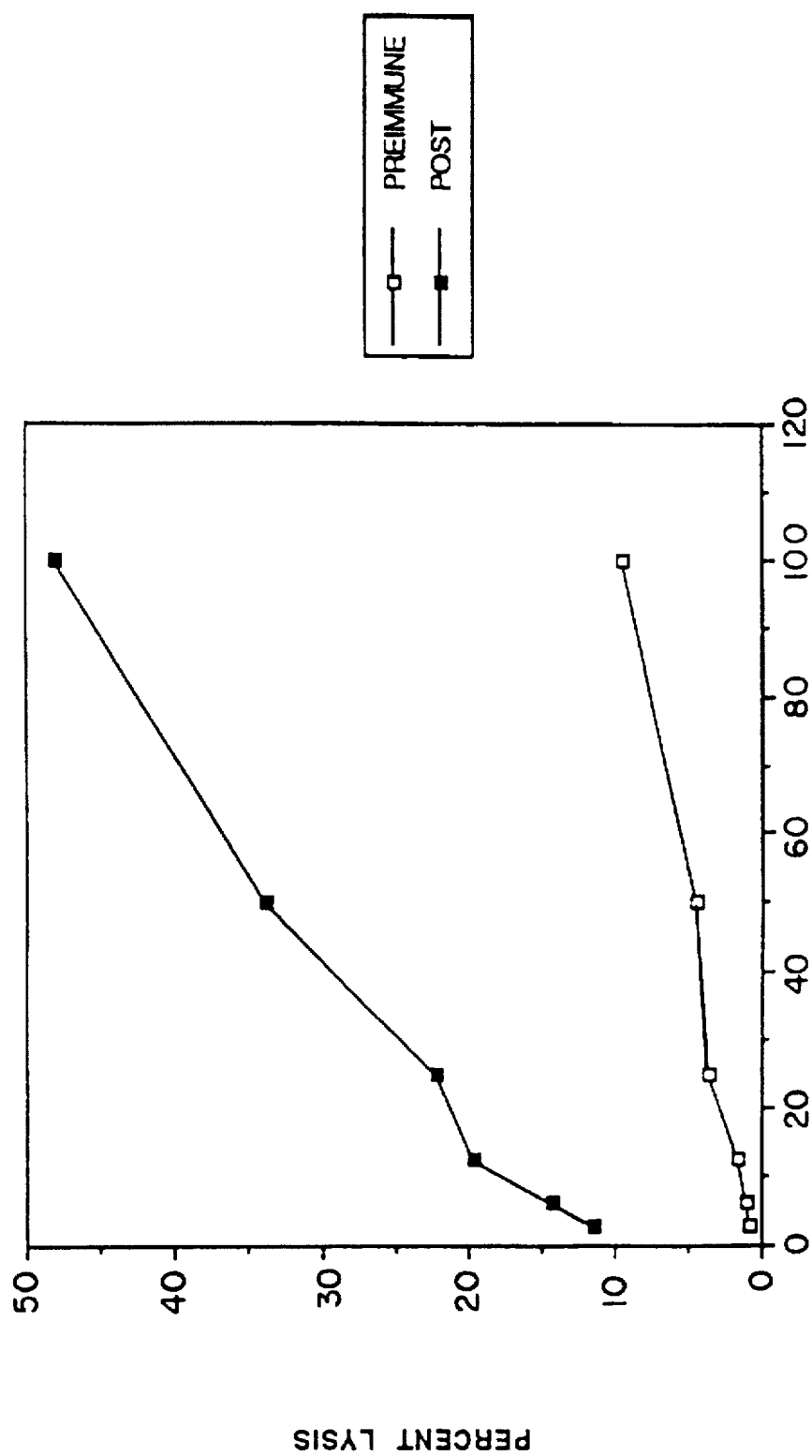

Biological activity of the immunoglobulins induced by the rV(NYC)-CEA vaccine was analyzed by antibody dependent cytotoxicity assays using human peripheral blood mononuclear cells as effectors and human CEA-transduced murine tumor cell lines as targets. Nontransduced cells were used as controls. As shown in FIG. 15A, specific lysis of the CEA expressing tumor cells was seen using serum from a monkey immunized with rV(NYC)-CEA while no lysis was observed using nontransduced tumor cells as targets. No lysis was seen with pre-immune sera or sera from a monkey inoculated with V-NYC. As shown in FIG. 15B the ADCC activity of the sera from rV(NYC)-CEA immunized monkeys was enhanced using IL-2 activated human peripheral blood mononuclear cells.

Cellular immune responses induced by rV(NYC)-CEA were assessed by delayed-type hypersensitivity (DTH) responses and lymphoproliferative assays. The DTH responses were assessed by skin testing 7 days following the last immunization. Purified CEA (Vitro Diagnostics, Littleton, Colo.) and ovalbumin (Sigma, St. Louis, Mo.) were intradermally injected at 100 μg in 0.1 ml of PBS. As a positive control, $1 \times 10^7$ PFU of UV-inactivated vaccinia virus (254 nm for 10 min) was injected. Swelling and erythema were measured 48 h later, and punch biopsies taken of positive responses and the DTH nature of the reaction confirmed by histopathological examination. The results showed that all seven monkeys receiving rV(NYC)-CEA as immunogen and four of five receiving the control V-NYC as immunogen responded with a positive DTH to the injection of inactivated V-NYC vaccinia virus, whereas none of the twelve monkeys responded to the ovalbumin control antigen challenge. None of the monkeys inoculated with V-NYC responded to CEA as challenge antigen while seven of eight monkeys immunized with the rV(NYC)-CEA responded with DTH reactions to the injections of CEA antigen. These results are depicted in FIG. 16.

For lymphoproliferative assays, PBMCs were isolated from immunized monkeys six or twelve months after their final immunization. PBMCs were isolated from heparinized blood using Lymphocyte Separation Medium, and PBMCs were cultured by plating $2 \times 10^5$ cells per well in 0.2 ml of RPMI 1640 supplemented with 10% heat-inactivated fetal calf serum in flat bottomed 96 well plates (Costar, Cambridge, Mass.) for 6 days with the appropriate antigen or for 3 days with Concanavalin A (Con A; Sigma). Cells were labeled for the final 18–24 h of incubation with 1 μCi per well of [$^3$H]-thymidine (New England Nuclear) and harvested with a PHD cell harvester (Cambridge Technology, Cambridge, Mass.). The incorporated radioactivity was measured by liquid scintillation spectroscopy (Beckman LS 3801), and the results from triplicate wells averaged and reported as the mean±SEM.

The results, shown in Table 7, indicated that all monkeys responded well, regardless of whether they received rV(NYC)-CEA or V-NYC. Little or no lymphocyte responses specific for CEA as compared to ovalbumin was seen from the monkeys immunized with V-NYC. Differential responses to CEA versus ovalbumin, however, were seen in the three monkeys immunized with rV(NYC)-CEA even at 12 months following the last immunization. These results and the DTH results thus demonstrate the ability of the rV(NYC)-CEA vaccine to elicit specific cellular responses to CEA.

TABLE 7

Lymphoproliferation Responses by PBMC of Rhesus Monkeys Immunized with V-NYC or rV(NYC)-CEA

| | Months Post | | $^3$H-Thymidine Incorporation (cpm)[2] | | | | |
|---|---|---|---|---|---|---|---|
| Monkey | Final Immunization | Immunogen[1] | Media | ConA | Vaccinia | CEA | Ovalbumin |
| 3 | 6 | rV(NYC)-CEA | 3,665 ± 291 | 84,039 ± 3,800 | 12,307 ± 818 | 7,504 ± 533 | 4,153 ± 689 |
| 9 | 6 | rV(NYC)-CEA | 1,833 ± 203 | 274,247 ± 8,571 | 19,473 ± 1,525 | 7,097 ± 829 | 1,206 ± 104 |
| 4 | 12 | rV(NYC)-CEA | 2,068 ± 221 | 394,365 ± 19,506 | 47,874 ± 4,487 | 15,902 ± 913 | 5,570 ± 434 |
| 7 | 6 | V-NYC | 3,807 ± 542 | 207,025 ± 6,328 | 11,903 ± 940 | 3,296 ± 225 | 3,355 ± 149 |
| 8 | 6 | V-NYC | 7,200 ± 654 | 502,662 ± 8,107 | 23,796 ± 611 | 9,486 ± 580 | 8,542 ± 460 |
| 1 | 12 | V-NYC | 5,189 ± | 360,253 ± | 23,120 ± | 7,867 ± | 5,088 ± |

TABLE 7-continued

Lymphoproliferation Responses by PBMC of
Rhesus Monkeys Immunized with V-NYC or rV(NYC)-CEA

| Monkey | Months Post Final Immunization | Immunogen[1] | $^3$H-Thymidine Incorporation (cpm)[2] | | | | |
|---|---|---|---|---|---|---|---|
| | | | Media | ConA | Vaccinia | CEA | Ovalbumin |
| | | | 616 | 2,928 | 2,125 | 250 | 481 |

[1]Rhesus monkeys were inoculated with 5 × 10$^8$ PFU of rV(NYC)-CEA or V-NYC on 3 (monkeys 9, 7, 8) or 4 (monkeys 3, 4, 1) separate occasions separated 6 weeks apart. PPBMC were then isolated from immunized monkeys 6 months (monkeys 3, 9, 7, 8) or 12 months (4, 1) after their final exposure.
[2]PBMC (2 × 10$^5$/well) were incubated without (medium control) or with various stimuli: Con A (2 μg/ml), UV-inactivated V-NYC (1 × 10$^7$ PFU/ml), purified CEA (100 μg/ml) or purified ovalbumin (100 μg/ml), for up to 3 days for Con A or 6 days for other antigens. Data are reported as the mean ± SEM of triplicate wells.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A recombinant virus comprising a vaccinia virus into which a carcinoembryonic antigen (CEA) gene is inserted which recombinant virus expresses CEA on the surface of cells infected therewith and which recombinant virus elicits a cell medicated immune response in vivo directed against CEA and cells expressing CEA.

2. The recombinant virus according to claim 1, wherein said vaccinia virus is of a V-WR strain.

3. The recombinant virus according to claim 1, wherein said vaccinia virus is of a NYC strain.

4. The recombinant virus according to claim 1, wherein said vaccinia virus is recombined with an attenuated human vaccinia virus strain.

5. The recombinant virus according to claim 1, wherein said CEA comprises a single or multiple immunodominant T-cell epitope.

6. A recombinant-carcinoembryonic antigen/vaccinia virus consisting of rV-CEA (ATCC accession no. VR 2323).

7. The recombinant virus according to claim 1, wherein said vaccinia virus contains a promoter that increases CEA expression.

8. A method of treating a carcinoma bearing patient wherein cells of said carcinoma express CEA which comprises administering to said patient the recombinant virus according to claim 1 to induce a cell mediated immune response to CEA.

9. The method according to claim 8, wherein said carcinoma cells are gastrointestinal, breast, pancreatic, bladder, ovarian, lung, or prostate carcinoma cells.

10. The method according to claim 8, wherein said carcinoma cells comprise epithelial derived carcinoma cells expressing CEA epitopes.

11. The method according to claim 8 further comprising administering with said recombinant virus a biological response modifier.

12. The method according to claim 11, wherein said biological response modifier is selected from the group consisting of interleukin-2 (IL-2), interleukin-6 (IL-6), interferon, tumor necrosis factor (TNF), and cyclophosphamide.

13. The method according to claim 8 further comprising administering with said recombinant virus an adjuvant.

14. A recombinant virus comprising a virus selected from the group consisting of baculovirus, human adenovirus, SV40, avian pox virus, and bovine papilloma virus into which a carcinoembryonic antigen (CEA) gene is inserted which recombinant virus expresses CEA on the surface of cells infected therewith and which recombinant virus elicits a cell medicated immune response in vivo directed against CEA or cells expressing CEA.

15. A method of treating a carcinoma bearing patient wherein cells of said carcinoma express CEA comprising administering to said patient the recombinant virus according to claim 14.

16. A method of stimulating the immune system of a primate against CEA for the purpose of preventing the establishment and growth of CEA-expressing carcinoma cells comprising administering to said primate the recombinant virus according to claim 1 in an amount sufficient to effect said stimulation.

17. The method according to claim 16, wherein said vaccinia virus is of the NYC strain.

18. The method according to claim 16, wherein the vaccinia virus is recombined with an attenuated human vaccinia virus strain.

19. The method according to claim 16 further comprising administering with said recombinant virus a biological response modifier.

20. The method of claim 19, wherein said biological response modifier is selected from the group consisting of interleukin-2 (IL-2), interleukin-6 (IL-6), interferon, tumor necrosis factor (TNF), and cyclophosphamide.

21. The method according to claim 16 further comprising administering with said recombinant virus an adjuvant.

22. A method of stimulating the immune system of a primate against CEA for the purpose of preventing the establishment and growth of CEA-expressing carcinoma cells comprising administering to said primate the recombinant virus according to claim 14 in an amount sufficient to effect said stimulation.

23. A pharmaceutical composition comprising the recombinant virus of claim 1, and a pharmaceutically acceptable diluent, carrier, or excipient carrier.

24. A pharmaceutical composition comprising the recombinant virus of claim 14, and a pharmaceutically acceptable diluent, carrier, or excipient carrier.

25. A recombinant pox virus for eliciting a cell mediated immune response in a human against carcinoembryonic antigen (CEA), comprising a virus suitable for immunization of a human and including a human CEA encoding gene inserted in the genome of said virus such that the recombinant pox virus expresses CEA on the surface of cells infected therewith and which recombinant virus elicits an immune response directed against CEA or cells expressing CEA.

26. The recombinant virus of claim 25, which is a vaccinia virus.

27. The recombinant virus of claim 25, which is an avian pox virus.

28. A method for stimulating the immune system of an individual against CEA to inhibit the establishment and growth of CEA-expressing carcinoma cells in said individual, comprising:

administering to the individual, in an amount sufficient to effect an immune response against said carcinoma cells, a recombinant virus suitable for immunization of a human which includes a gene encoding CEA inserted in the genome of said virus such that the recombinant virus expresses CEA on the surface of cells infected therewith and which recombinant virus elicits an immune response directed against CEA or cells expressing CEA.

29. The method of claim 28, wherein the virus is a human adenovirus, bovine papilloma virus, or a poxvirus.

30. The method of claim 29, wherein the poxvirus is a vaccinia virus.

31. The method of claim 29, wherein the poxvirus is an avian pox virus.

32. A method of generating an immune response against carcinoembryonic antigen (CEA) in a human comprising administering a sufficient amount of a recombinant virus to generate a CEA-specific cell-mediated immune response wherein the recombinant virus contains a CEA encoding gene inserted in the genome of said recombinant virus, such that the recombinant virus expresses CEA in a cell infected therewith.

33. The method of claim 32, wherein the recombinant virus is a pox virus.

34. The method of claim 33, wherein the pox virus is a vaccinia virus.

35. The method of claim 33, wherein the pox virus is an avipox virus.

* * * * *